(12) United States Patent
Kirchhofer et al.

(10) Patent No.: US 8,124,352 B2
(45) Date of Patent: Feb. 28, 2012

(54) METHODS AND COMPOSITIONS FOR TARGETING HEPSIN

(75) Inventors: Daniel K. Kirchhofer, Los Altos, CA (US); Rajesh Vij, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 141 days.

(21) Appl. No.: 12/306,208

(22) PCT Filed: Jun. 20, 2007

(86) PCT No.: PCT/US2007/071688
§ 371 (c)(1),
(2), (4) Date: Oct. 6, 2009

(87) PCT Pub. No.: WO2007/149932
PCT Pub. Date: Dec. 27, 2007

(65) Prior Publication Data
US 2010/0021474 A1 Jan. 28, 2010

Related U.S. Application Data

(60) Provisional application No. 60/805,589, filed on Jun. 22, 2006.

(51) Int. Cl.
*C07K 16/18* (2006.01)
*C07K 16/28* (2006.01)
*C12N 5/10* (2006.01)
*C12N 15/13* (2006.01)
*G01N 33/53* (2006.01)

(52) U.S. Cl. ......... 435/7.1; 435/326; 435/328; 435/338; 435/344; 435/69.1; 530/387.1; 530/388.1; 530/388.26; 530/388.8; 536/23.53

(58) Field of Classification Search .................. None
See application file for complete search history.

(56) References Cited

U.S. PATENT DOCUMENTS

| | | | |
|---|---|---|---|
| 5,981,830 A | 11/1999 | Wu et al. | |
| 6,423,543 B1 | 7/2002 | Marcotte et al. | |
| 6,482,630 B2 | 11/2002 | Gan et al. | |
| 2003/0013097 A1 | 1/2003 | Welsh et al. | |
| 2003/0049645 A1 | 3/2003 | Mu et al. | |
| 2003/0175736 A1 | 9/2003 | Chinnaiyan et al. | |
| 2003/0223973 A1 | 12/2003 | O'Brien et al. | |
| 2004/0001801 A1 | 1/2004 | Madison et al. | |
| 2004/0009911 A1 | 1/2004 | Harris et al. | |
| 2004/0132156 A1 | 7/2004 | Parry et al. | |

FOREIGN PATENT DOCUMENTS

WO   WO 01/57194 A2   8/2001

(Continued)

OTHER PUBLICATIONS

Rudikoff et al., Single amino acid substitution altering antigen-binding specificity, Proc. Nat. Acad. Sci. USA, 79:1979-1983, 1982.*

(Continued)

*Primary Examiner* — Lorraine Spector
*Assistant Examiner* — Claire Kaufman
(74) *Attorney, Agent, or Firm* — Stephanie Yonker

(57) ABSTRACT

Anti-HEPSIN monoclonal antibodies, and methods for using the antibodies, are provided.

16 Claims, 11 Drawing Sheets

FOREIGN PATENT DOCUMENTS

| | | |
|---|---|---|
| WO | WO 01/57194 A3 | 8/2001 |
| WO | WO 01/62271 A1 | 8/2001 |
| WO | WO 02/059373 A2 | 8/2002 |
| WO | WO 02/064839 A2 | 8/2002 |
| WO | WO 03/016484 | 2/2003 |
| WO | WO 03/064620 A2 | 8/2003 |
| WO | WO 03/064620 A3 | 8/2003 |
| WO | WO 2004/009803 | 1/2004 |
| WO | WO 2004/033630 | 4/2004 |
| WO | WO 2004/035733 A2 | 4/2004 |
| WO | WO 2004/035733 A3 | 4/2004 |
| WO | WO 2006/014928 A1 | 2/2006 |
| WO | WO 2007/149932 A2 | 12/2007 |
| WO | WO 2007/149935 A2 | 12/2007 |

OTHER PUBLICATIONS

MacCallum et al., Antibody-antigen interactions: contact analysis and binding site topography, J. Mol. Biol. 262:732-745, 1996.*
Lamminnaki et al., Crystal structure of a recombinant anti-estradiol Fab fragment in complex with 17Beta-estradiol, J. Biol. Chem. 276(39):36687-36694, Sep. 28, 2001.*
Adachi et al., "Activation of Epithelial Sodium Channels by Prostasin in Xenopus Oocytes" *J Am Soc Nephrol* 12(6):1114-1121 (2001).
Andreasen, P. A. et al., "The urokinase-type plasminogen activator system in cancer metastasis: a review" *Int. J. Cancer* 72:1-22 (1997).
Bachmann. F., "The plasminogen-plasmin enzyme system" *Hemostasis and Thrombosis: Basic Principles and Clinical Practice*, Colman, R.W. et al., Third Edition, Lippincott Company, Philadelphia, Chapter 84, pp. 1592-1622 (1994).
Benaud et al., "Regulation of the activity of matriptase on epithelial cell surfaces by a blood-derived factor" *Eur J Biochem* 268(5):1439-1447 (2001).
Birchmeier et al., "Met, Metastasis, Motility and More" *Nature Reviews Molecular Cell Biology* 4:915-925 (Dec. 2003).
Bouton et al., "The Serpin Protease-Nexin 1 is Present in Rat Aortic Smooth Muscle Cells and is Upregulated in L-NAME Hypertensive Rats" *Arterioscler Thromb Vasc Biol* 23(1):142-147 (Jan. 2003).
Brunner, G. et al., "A T-cell-related proteinase expressed by T-lymphoma cells activates their endogenous pro-urokinase" *Blood* 79(8):2099-2106 (Apr. 15, 1992).
Carmeliet et al., "Physiological consequences of loss of plasminogen activator gene function in mice" *Nature* 368(6470):419-424 (1994).
Chen et al., "Down-Regulation of Prostasin Serine Protease: A Potential Invasion Suppressor in Prostate Cancer" *Prostate* 48(2):93-103 (Jun. 15, 2001).
Chen et al., "Prostasin is a Glycosylphosphatidylinositol-anchored Active Serine Protease" *J Biol Chem* 276(24):21434-21442 (2001).
Chen et al., "Prostasin Serine Inhibits Breast Cancer Invasiveness and is Transcriptionally Regulated by Promoter DNA Methylation" *Int. J Cancer* 97(3):323-329 (2002).
Chen et al., "Regulation of Prostasin Expression and Function in the Prostate" *Prostate* 59(1):1-12 (2004).
Chen, Z. et al., "Hepsin and maspin are inversely expressed in laser capture microdissectioned prostate cancer" *J. Urol.* 169:1316-1319 (Apr. 2003).
Cheng and Prusoff, "Relationship between the inhibition constant ($K_I$) and the concentration of inhibitor which causes 50 per cent inhibition ($I_{50}$) of an enzymatic reaction" *Biochem. Pharmacol.* 22:3099-3108 (1973).
Collen, D. et al., "Activation of plasminogen by pro-urokinase" *Journal of Biological Chemistry* 261(3):1259-1266 (Jan. 25, 1986).
Dano, K. et al., "Plasminogen activation and cancer" *Thromb. Haemost.* 93:676-681 (2005).
Delaria et al., "Characterization of placental bikunin, a novel human serine protease inhibitor" *J Biol Chem.* 272(18):12209-12214 (May 2, 1997).
Denda et al., "Functional characterization of Kunitz domains in hepatocyte growth factor activator inhibitor type 1" *J Biol Chem.* 277(16):14053-14059 (Apr. 19, 2002).
Dennis and Lazarus, "Kunitz Domain Inhibitors of Tissue Factor-Factor VIIa; I. Potent Inhibitors Selected from Libraries by Phage Display" *Journal of Biological Chemistry* 269(35):22129-22136 (1994).
Dennis et al., "Potent and selective Kunitz domain inhibitors of plasma kallikrein designed by phage display" *J Biol Chem.* 270(43):25411-25417 (Oct. 27, 1995).
Dhanasekaran et al., "Delineation of prognostic biomarkers in prostate cancer" *Nature* 412(6849):822-826 (Aug. 23, 2001).
Donaldson et al., "Regulation of the Epithelial Sodium Channel by Serine Proteases in Human Airways" *J Biol Chem.* 277(10):8338-8345 (Mar. 8, 2002).
Fan, B. et al., "Identification of hepatocyte growth factor activator inhibitor 1-B as a potential physiological inhibitor of prostasin" *Journal of Biological Chemistry* 280(41):34513-34520 (Oct. 14, 2005).
Gailani et al., "A murine model of factor XI deficiency" *Blood Coag. Fibrinol.* 8:134-144 (1997).
Gak et al., "Processing of Hepatocyte Growth Factor to the Heterodimeric Form is Required for Biological Activity" *FEBS Letters* 311(1):17-21 (Oct. 1992).
Gmyrek et al., "Normal and malignant prostate epithelial cells differ in their response to hepatocyte growth factor/scatter factor" *Am J Pathol.* 159(2):579-590 (Aug. 2001).
Goretzki, L. et al., "Effective activation of the proenzyme form of the urokinase-type plasminogen activator (pro-uPA) by the cysteine protease cathepsin L" *FEBS Letters* 297(1, 2):112-118 (Feb. 1992).
Graeber and Eisenberg, "Bioinformatic Identification of Potential Autocrine Signaling Loops in Cancers from Gene Expression Profiles" *Nat. Genet.* 29(3):295-300 (Nov. 2001).
Haab, Brian B., "Antibody arrays in cancer research" *Mol. & Cellular Proteomics* 4(4):377-383 (2005).
Hall, C. L. et al., "Enhanced invasion of hormone refractory prostate cancer cells through hepatocyte growth factor (HGF) induction of urokinase-type plasminogen activator (u-PA)" *Prostate* 59:167-176 (2004).
Hamasuna, R. et al., "Reduced expression of hepatocyte growth factor activator inhibitor type-2/placental bikunin (HAI-2/PB) in human glioblastomas: implication for anti-invasive role of HAI-2/PB in glioblastoma cells" *Int. J. Cancer* 93:339-345 (2001).
Hartmann et al., "A Functional Domain in the Heavy Chain of Scatter Factor/Hepatocyte Growth Factor Binds the c-Met Receptor and Induces Cell Dissociation but Not Mitogenesis" *Proc. Natl. Acad. Sci. USA* 89(23):11574-11578 (Dec. 1, 1992).
Hathaway et al., "Clinical and physiologic studies of two siblings with prekallikrein (Fletcher factor) deficiency" *Am J Med.* 60(5):654-664 (May 10, 1976).
Helenius, M. A. et al., "Amplification of urokinase gene in prostate cancer" *Cancer Research* 61:5340-5344 (Jul. 15, 2001).
Herter, S. et al., "Hepatocyte growth factor is a preferred in vitro substrate for human hepsin, a membrane-anchored serine protease implicated in prostate and ovarian cancers" *Biochemical Journal* 390:125-136 (Apr. 20, 2005).
Hongo, J. S. et al., "Development and characterization of murine monoclonal antibodies to the latency-associated peptide of transforming growth factor β1" *Hybridoma* 14(3):253-260 (1995).
Huai, Q. et al., "Structure of human urokinase plasminogen activator in complex with its receptor" *Science* 311:656-659 (Feb. 3, 2006).
Huntsman, D. et al., "Comparison of c-met expression in ovarian epithelial tumors and normal epithelia of the female reproductive tract by quantitative laser scan microscopy" *Am. J. Pathol.* 155(2):343-348 (Aug. 1999).
Husten et al., "The active site of blood coagulation factor Xa. Its distance from the phospholipid surface and its conformational sensitivity to components of the prothrombinase complex" *J Biol Chem.* 262(27):12953-12961 (Sep. 25, 1987)
Ichinose, A. et al., "The activation of pro-urokinase by plasma kallikrein and its inactivation by thrombin" *Journal of Biological Chemistry* 261(8):3486-3489 (Mar. 15, 1986).
International Preliminary Report on Patentability for International Patent Application No. PCT/US2007/071688.
International Preliminary Report on Patentability for International Patent Application No. PCT/US2007/071691.
International Search Report and Written Opinion for International Patent Application No. PCT/US2007/071688.
Itoh et al., "Genomic Structure and Chromosomal Localization of the Human Hepatocyte Growth Factor Activator Inhibitor Type 1 and 2 Genes" *Eur J Biochem* 267(11):3351-3359 (2000).

Itoh et al., "Upregulation of HGF Activator Inhibitor Type 1 but not Type 2 along with Regeneration of Intestinal Mucosa" *Am J Physiol Gastrointest Liver Physiol.* 278(4):G635-643 (Apr. 2000).

Jin, J. et al., "Increasing expression of serine protease matriptase in ovarian tumors: tissue microarray analysis of immunostaining score with clinicopathological parameters" *Modern Pathology* 19:447-452 (2006).

Johnson, M.D. et al., "Possible role of matriptase in the diagnosis of ovarian cancer" *Expert Rev. Mol. Diagn.* 3(3):331-338 (2003).

Kataoka et al., "Activation of Hepatocyte Growth Factor/Scatter Factor in Colorectal Carcinoma" *Cancer Research* 60:6148-6159 (Nov. 1, 2000).

Kataoka et al., "Distribution of hepatocyte growth factor activator inhibitor type 1 (HAI-1) in human tissues: Cellular surface localization of HAI-1 in simple columnar epithelium and its modulated expression in injured and regenerative tissues" *J Histochem Cytochem.* 47(5):673-682 (May 1999).

kataoka et al., "Evaluation of hepatocyte growth factor activator inhibitor expression in normal and malignant colonic mucosa" *Cancer Lett.* 128(2):219-227 (Jun. 19, 1998).

Kataoka et al., "Hepatocyte growth factor activator inhibitor type 1 is a specific cell surface binding protein of hepatocyte growth factor activator (HGFA) and regulates HGFA activity in the pericellular microenvironment" *J Biol Chem* 275(51):40453-40462 (2000).

Kataoka et al., "Roles of Hepatocyte Growth Factor (HGF) Activator and HGF Activator Inhibitor in the Pericellular Activation of HGF/Scatter Factor" *Cancer Metastasis Rev* 22(2):223-236 (2003).

Kataoka, H. et al., "Conserved expression of hepatocyte growth factor activator inhibitor type-2/placental bikunin in human colorectal carcinomas" *Cancer Lett.* 148:127-134 (2000).

Kawaguchi et al., "Purification and cloning of hepatocyte growth factor activator inhibitor type 2, a Kunitz-type serine protease inhibitor" *J Biol Chem.* 272(44):27558-27564 (Oct. 31, 1997).

Kazama et al., "Hepsin, a putative membrane-associated serine protease, activates human factor VII and initiates a pathway of blood coagulation on the cell surface leading to thrombin formation" *J Biol Chem.* 270(1):66-72 (Jan. 6, 1995).

Kelley et al., "Similar molecular interactions of factor VII and factor VIIa with the tissue factor region that allosterically regulates enzyme activity" *Biochemistry* 43(5):1223-1229 (Feb. 10, 2004).

Kirchhofer et al., "Hepsin activates pro-hepatocyte growth factor and is inhibited by hepatocyte growth factor activator inhibitor-1B (HAI-1B) and HAI-2" *FEBS Letters* 579(9):1945-1950 (Mar. 28, 2005).

Kirchhofer et al., "Structural and functional basis of the serine protease-like hepatocyte growth factor beta-chain in Met binding and signaling" *J Biol Chem.* 279(38):39915-39924 (Sep. 17, 2004).

Kirchhofer et al., "Tissue expression, protease specificity, and Kunitz domain functions of hepatocyte growth factor activator inhibitor-1B (HAI-1B), a new splice variant of HAI-1" *J Biol Chem.* 278(38):36341-36349 (Sep. 19, 2003).

Klezovitch, O. et al., "Hepsin promotes prostate cancer progression and metastasis" *Cancer Cell* 6:185-195 (Aug. 2004).

Knudsen and Edlund, "Prostate cancer and the met hepatocyte growth factor receptor" *Advances in Cancer Res.* 91:31-67 (2004).

Knudsen, B. et al., "High expression of the Met receptor in prostate cancer metastasis to bone" *Urology* 60:1113-1117 (2002).

Kobayashi, H. et al., "Cathepsin B efficiently activates the soluble and the tumor cell receptor-bound form of the proenzyme urokinase-type plasminogen activator (Pro-uPA)" *Journal of Biological Chemistry* 266(8):5147-5152 (Mar. 15, 1991).

Kohler and Milstein, "Continuous cultures of fused cells secreting antibody of predefined specificity"*Nature* 256:495-497 (Aug. 7, 1975).

Landers, K.A. et al., "Use of multiple biomarkers for a molecular diagnosis of prostate cancer" *Int. J. Cancer* 114:950-956 (2005).

Lee, S. et al., "Activation of hepatocyte growth factor and urokinase/plasminogen activator by matriptase, an epithelial membrane serine protease" *Journal of Biological Chemistry* 275(47):36720-36725. (Nov. 24, 2000).

Leytus et al., "A novel trypsin-like serine protease (hepsin) with a putative transmembrane domain expressed by human liver and hepatoma cells" *Biochemistry* 27(3):1067-1074 (Feb. 9, 1988).

Lijnen, H.R. et al., "Activation with plasmin of two-chain urokinase-type plasminogen activator derived from single-chain urokinase-type plasminogen activator by treatment with thrombin" *European Journal of Biochemistry* 169:359-364 (1987).

Lin et al., "Characterization of a Novel, Membrane-Bound, 80-kDa Matrix-Degrading Protease from Human Breast Cancer Cells. Monoclonal Antibody Production, Isolation, and Localization" *J Biol Chem* 272(14):9147-9152 (Apr. 4, 1997).

Lin et al., "Molecular cloning of cDNA for matriptase, a matrix-degrading serine protease with trypsin-like activity" *J Biol Chem.* 274(26):18231-18236 (Jun. 25, 1999).

Lin et al., "Purification and characterization of a complex containing matriptase and a kunitz-type serine protease inhibitor from human milk" *J Biol Chem* 274(26):18237-18242 (Jun. 25, 1999).

List, K. et al., "Deregulated matriptase causes ras-independent multistage carcinogenesis and promotes ras-mediated malignant transformation" *Genes & Development* 19:1934-1950 (2005).

List, K. et al., "Matriptase/MT-SP1 is required for postnatal survival, epidermal barrier function, hair follicle development, and thymic homeostasis" *Oncogene* 21:3765-3779 (2002).

List, K. et al., "Plasminogen-independent initiation of the pro-urokinase activation cascade in vivo. Activation of pro-urokinase by glandular kallikrein (mGK-6) in plasminogen-deficient mice" *Biochemistry* 39:508-515 (2000).

Liu et al., "NetAffx: Affymetrix Probesets and Annotations" *Nucleic Acids Res* 31(1):82-86 (2003).

Lokker et al., "Structure-Function Analysis of Hepatocyte Growth Factor: Identification of Variants that Lack Mitogenic Activity Yet Retain High Affinity Receptor Binding" *EMBO Journal* 11(7):2503-2510 (1992).

Luo et al., "Human prostate cancer and benign prostatic hyperplasia: molecular dissection by gene expression profiling" *Cancer Research* 61(12):4683-4688 (Jun. 15, 2001).

Magee et al., "Expression profiling reveals hepsin overexpression in prostate cancer" *Cancer Research* 61(15):5692-5696 (Aug. 1, 2001).

Mann, K.G., "Biochemistry and Physiology of Blood Coagulation" *Thrombosis and Haemostasis* 82:165-174 (1999).

Marlor et al., "Identification and cloning of human placental bikunin, a novel serine protease inhibitor containing two Kunitz domains" *J Biol Chem.* 272(18):12202-12208 (May 2, 1997).

McCallum et al., "The location of the active site of blood coagulation factor VIIa above the membrane surface and its reorientation upon association with tissue factor. A fluorescence energy transfer study" *J Biol Chem.* 271(45):28168-28175 (Nov. 8, 1996).

Mimms et al., "Phospholipid Vesicle Formation and Transmembrane Protein Incorporation Using Octyl Glucoside" *Biochemistry* 20(4):833-840 (1981).

Miyazawa, K. et al., "Molecular cloning and sequence analysis of the cDNA for a human serine protease responsible for activation of hepatocyte growth factor" *Journal of Biological Chemistry* 268(14):10024-10028 (May 15, 1993).

Mok, S.C. et al., "Prostasin, a Potential Serum Marker for Ovarian Cancer: Identification Through Microarray Technology" *J National Cancer Inst.* 93(19):1458-1464 (Oct. 3, 2001).

Moran, P. et al., "Pro-urokinase-type plasminogen activator is a substrate for hepsin" *J Biol. Chem.* 281(41):30439-30446 (Oct. 13, 2006).

Morrison, J.F., "Kinetics of the reversible inhibition of enzyme-catalysed reactions by tight-binding inhibitors" *Biochimica Et Biophysica Acta* 185:269-286 (1969).

Muthukumar, T. et al., "Serine Proteinase Inhibitor-9, an Endogenous Blocker of Granzyme B/Perforin Lytic Pathway, is Hyperexpressed during Acute Rejection of Renal Allografts" *Transplantation* 75(9):1565-1570 (May 15, 2003).

Mutucumarana et al., "The active site of factor IXa is located far above the membrane surface and its conformation is altered upon association with factor VIIIa. A fluorescence study" *J Biol Chem.* 267(24):17012-17021 (Aug. 25, 1992).

Naka, D. et al., "Activation of Hepatocyte Growth Factor by Proteolytic Conversion of a Single Chain Form to a Heterodimer" *Journal of Biological Chemistry* 267(28):20114-20119 (Oct. 5, 1992).

Naldini et al., "Extracellular Proteolytic Cleavage by Urokinase is Required for Activation of Hepatocyte Growth Factor/Scatter Factor" *EMBO Journal* 11(13):4825-4833 (Dec. 1992).

Nauland and Rijken, "Activation of thrombin-inactivated single-chain urokinase-type plasminogen activator by dipeptidyl peptidase I (cathepsin C)" *European Journal of Biochemistry* 223:497-501 (1994).

Ngo, J. Thomas et al., "Computational Complexity, Protein Structure Prediction, and the Levinthal Paradox" *The Protein Folding Problem and Tertiary Structure Prediction*, K. Merz, Jr. and S. Le Grand, Boston:Birkhauser, Chapter 14, pp. 433-506 (1994).

Oberst et al., "Expression of the serine protease matriptase and its inhibitor HAI-1 in epithelial ovarian cancer: correlation with clinical outcome and tumor clinicopathological parameters" *Clin Cancer Res.* 8(4):1101-1107 (Apr. 2002).

Oberst et al., "Matriptase and HAI-1 are expressed by normal and malignant epithelial cells in vitro and in vivo" *Am J Pathol.* 158(4):1301-1311 (Apr. 2001).

Okigaki et al., "Functional Characterization of Human Hepatocyte Growth Factor Mutants Obtained by Deletion of Structural Domains" *Biochemistry* 31(40):9555-9561 (Oct. 13, 1992).

Olivero, A. G. et al., "A selective, slow binding inhibitor of factor VIIa binds to a nonstandard active site conformation and attenuates thrombus formation in vivo" *Journal of Biological Chemistry* 280(10):9160-9169 (Mar. 11, 2005).

Parr and Jiang, "Expression of hepatocyte growth factor/scatter factor, its activator, inhibitors and the c-Met receptor in human cancer cells" *Int. J. Oncol.* 19:857-863 (2001).

Peek et al., "Unusual Proteolytic Activation of Pro-hepatocyte Growth Factor by Plasma Kallikrein and Coagulation Factor XIa" *Journal of Biological Chemistry* 277(49):47804-47809 (Dec. 6, 2002).

Petersen, L. C. et al., "One-chain urokinase-type plasminogen activator from human sarcoma cells is a proenzyme with little or no intrinsic activity" *Journal of Biological Chemistry* 263(23):11189-11195 (Aug. 15, 1988).

Phillips et al., "A role for the Granzyme B Inhibitor Serine Protease Inhibitor 6 in CD8+ Memory Cell Homeostasis" *J Immunol.* 173(6):3801-3809 (2004).

Qin et al., "Functional characterization of Kunitz domains in hepatocyte growth factor activator inhibitor type 2" *FEBS Letters* 436(1):111-114 (Sep. 25, 1998).

Rapaport and Rao, "The Tissue Factor Pathway: How It Has Become a "Prima Ballerina"" *Thrombosis and Haemostasis* 74:7-17 (1995).

Richard, B. et al., "Protease nexin-1: a cellular serpin down-regulated by thrombin in rat aortic smooth muscle cells" *J. Cell. Physiol.* 201:138-145 (2004).

Riddick, ACP et al., "Identification of degradome components associated with prostate cancer progression by expression analysis of human prostatic tissues" *British J. Cancer* 92:2171-2180 (2005).

Ried, S. et al., "Activation mechanisms of the urokinase-type plasminogen activator promoter by hepatocyte growth factor/scatter factor" *Journal of Biological Chemistry* 274(23):16377-16386 (Jun. 4, 1999).

Saleem, M. et al., "A novel biomarker for staging human prostate adenocarcinoma: overexpression of matriptase with concomitant loss of its inhibitor, hepatocyte growth factor activator inhibitor-1" *Cancer Epidemiol. Biomarkers Prev.* 15(2):217-227 (Feb. 2006).

Schmidt et al., "Scatter factor/hepatocyte growth factor is essential for liver development" *Nature* 373:699-702 (Feb. 23, 1995).

Sheng, Shijie, "The urokinase-type plasminogen activator system in prostate cancer metastasis" *Cancer and Metastasis Reviews* 20:287-296 (2001).

Shia, S. et al., "Conformational lability in serine protease active sites: structures of hepatocyte growth factor activator (HGFA) alone and with the inhibitory domain from HGFA inhibitor-1B" *J. Mol. Biol.* 346:1335-1349 (2005).

Shimomura et al., "Activation of hepatocyte growth factor by two homologous proteases, blood-coagulation factor XIIa and hepatocyte growth factor activator" *European Journal of Biochemistry* 229(1):257-261 (Apr. 1, 1995).

Shimomura, T. et al., "Hepatocyte growth factor activator inhibitor, a novel kunitz-type serine protease inhibitor" *Journal of Biological Chemistry* 272(10):6370-6376 (Mar. 7, 1997).

Shimomura, T. et al., "Multiple Sites of Proteolytic Cleavage to Release Soluble Forms of Hepatocyte Growth Factor Activator Inhibitor Type 1 from a Transmembrane Form" *J Biochem (Tokyo)* 126(5):821-828 (1999).

Shipway, A. et al., "Biochemical Characterization of Prostasin, a Channel Activating Protease" *Biochem Biophys Res Commun.* 324(2):953-963 (2004).

Somoza et al., "The structure of the extracellular region of human hepsin reveals a serine protease domain and a novel scavenger receptor cysteine-rich (SRCR) domain" *Structure* 11(9):1123-1131 (Sep. 2003).

Srikantan et al., "HEPSIN inhibits cell growth/invasion in prostate cancer cells" *Cancer Research* 62(23):6812-6816 (Dec. 1, 2002).

Stack and Johnson, "Human mast cell tryptase activates single-chain urinary-type plasminogen activator (Pro-urokinase)" *Journal of Biological Chemistry* 269(13):9416-9419 (Apr. 1, 1994).

Stamey et al., "Molecular genetic profiling of Gleason grade 4/5 prostate cancers compared to benign prostatic hyperplasia" *J Urol.* 166(6):2171-2177 (Dec. 2001).

Stamos et al., "Crystal structure of the HGF beta-chain in complex with the Sema domain of the Met receptor" *EMBO Journal* 23(12):2325-2335 (Jun. 16, 2004).

Stephan et al., "Hepsin is highly over expressed in and a new candidate for a prognostic indicator in prostate cancer" *J Urol.* 171(1):187-191 (Jan. 17, 2004).

Szabo et al., "Type II transmembrane serine proteases" *Thromb Haemost.* 90(2):185-193 (Aug. 2003).

Takahashi, S. et al., "Down-Regulated Expression of Prostasin in High-Grade or Hormone-Refractory Human Prostate Cancers" *Prostate* 54(3):187-193 (2003).

Takeuchi, T. et al., "Cellular localization of membrane-type serine protease 1 and identification of protease-activated receptor-2 and single-chain urokinase-type plasminogen activator as substrates" *Journal of Biological Chemistry* 275(34):26333-26342 (Aug. 25, 2000).

Takeuchi, T. et al., "Reverse biochemistry: Use of macromolecular protease inhibitors to dissect complex biological processes and identify a membrane-type serine protease in epithelial cancer and normal tissue" *Proc. Natl. Acad. Sci. USA* 96(20):11054-11061 (Sep. 28, 1999).

Tanimoto et al., "Hepsin, a cell surface serine protease identified in hepatoma cells, is overexpressed in ovarian cancer" *Cancer Research* 57(14):2884-2887 (Jul. 15, 1997).

Tong, Z. et al., "Prostasin, a Membrane-Anchored Serine Peptidase, Regulates Sodium Currents in JME/CF15 Cells, a Cystic Fibrosis Airway Epithelial Cell Line" *Am J Physiol Lung Cell Mol Physiol.* 287:L928-L935 (Nov. 2004).

Torres-Rosado et al., "Hepsin, a putative cell-surface serine protease, is required for mammalian cell growth" *Proc Natl Acad Sci U S A.* 90(15):7181-7185 (Aug. 1, 1993).

Trusolino et al., "Scatter-factor and semaphorin receptors: cell signalling for invasive growth" *Nat Rev Cancer* 2(4):289-300 (Apr. 2, 2002).

Tsuji et al., "Hepsin, a cell membrane-associated protease. Characterization, tissue distribution, and gene localization" *J Biol Chem.* 266(25):16948-16953 (Sep. 5, 1991).

Tyagi et al., "Co-Expression of Tissue Inhibitor and Matrix Metalloproteinase in Myocardium" *J Mol Cell Cardiol.* 27(10):2177-2189 (1995).

Uehara et al., "Placental defect and embryonic lethality in mice lacking hepatocyte growth factor/scatter factor" *Nature* 373:702-705 (Feb. 23, 1995).

Veldhuizen, V. et al., "Urokinase-type plasminogen activator expression in human prostate carcinomas" *Am. J. Med. Sci.* 312(1):8-11 (1996).

Vu et al., "Identification and cloning of the membrane-associated serine protease, hepsin, from mouse preimplantation embryos" *J Biol Chem.* 272(50):31315-31320 (Dec. 12, 1997).

Wells, James A., "Additivity of Mutational Effects in Proteins" Biochemistry 29:8509-8517 (1990) *Biochemistry* 29(37):8509-8517 (Sep. 18, 1990).

Welsh et al., "Analysis of gene expression identifies candidate markers and pharmacological targets in prostate cancer" *Cancer Research* 61(16):5974-5978 (Aug. 15, 2001).

Wolf, B. et al., "Nerve growth factor-γ activates soluble and receptor-bound single chain urokinase-type plasminogen activator" *J.Biol. Chem.* 268(22):16327-16331 (Aug. 5, 1993).

Wong et al., "Coexpression of hepatocyte growth factor-Met: an early step in ovarian carcinogenesis?" *Oncogene* 20(11):1318-1328 (Mar. 15, 2001).

Wu et al., "Generation and characterization of mice deficient in hepsin, a hepatic transmembrane serine protease" *J Clin Invest.* 101(2):321-326 (Jan. 15, 1998).

Xuan, J. et al., "Antibodies neutralizing hepsin protease activity do not impact cell growth but inhibit invasion of prostate and ovarian tumor cells in culture" *Cancer Research* 66(7):3611-3619 (Apr. 1, 2006).

Yamauchi et al., "Hepatocyte growth factor activator inhibitor types 1 and 2 are expressed by tubular epithelium in kidney and down-regulated in renal cell carcinoma" *J Urol.* 171(2 Pt 1):890-896 (Feb. 2004).

Yasuda, S. et al., "Urokinase-type plasminogen activator is a preferred substrate of the human epithelium serine protease tryptase ε/PRSS22" *Blood* 105(10):3893-3901 (May 15, 2005).

Yu et al., "Mice deficient in hepsin, a serine protease, exhibit normal embryogenesis and unchanged hepatocyte regeneration ability" *Thromb Haemost.* 84(5):865-870 (Nov. 2000).

Yu et al., "Molecular Cloning, Tissue-specific Expression, and Cellular Localization of Human Prostasin mRNA" *J Biol Chem.* 270(22):13483-13489 (Jun. 2, 1995).

Yu et al., "Prostasin is a Novel Human Serine Protenaise from Seminal Fluid Purification, Tissue Distribution, and Localization in Prostate Gland" *J Biol Chem.* 269(29):18843-18848 (Jul. 22, 1994).

Zacharski et al., "Expression of the factor VII activating protease, hepsin, in situ in renal cell carcinoma" *Thromb Haemost.* 79(4):876-877 (Apr. 1998).

Zhu et al., "Overexpression and regulation of expression of scatter factor/hepatocyte growth factor in prostatic carcinoma" *Urology* 56(6):1071-1074 (Dec. 20, 2000).

Zhukov et al., "Purification and characterization of hepsin from rat liver microsomes" *Biochim Biophys Acta.* 1337(1):85-89 (Jan. 4, 1997).

\* cited by examiner

FIG._1

| Cell Line | Isotype[3] | Epitope Group | Direct ELISA[4] | FACS (Median Fluorescence) | |
|---|---|---|---|---|---|
| | | | | LnCaP-34[1,5] +MAb (1μg/ml) | LnCaP-17[2,6] +MAb (1μg/ml) |
| 3H10.1.2 | κ, IgG1 | A | [+] | 113.4 | 30.2 |
| 2D5.1.9 | κ, IgG1 | B | [+] | 189.4 | 32.8 |
| 1F2.1.1 | κ, IgG2b | A | [+] | 86.6 | 10.6 |
| 1E7.1.1 | κ, IgG1 | C | [+] | 7.1 | 4.8 |
| 3H1.1.1 | κ, IgG2b | A | [+] | 112.4 | 10.6 |

[1] LnCaP-34: LnCaP co-transfected with luciferase and hepsin
[2] LnCaP-17: LnCaP overexpressing luciferase with endogenous hepsin
[3] Isostrip (Roche Diagnostics Corporation, IN, USA) and mono AB-ID SP kit (Zymed Laboratories, CA USA)
[4] Human hepsin-His8
[5] LnCaP-34 control median fluorescence: 6.3
[6] LnCaP-17 control median fluorescence: 4.5

FIG. 2

| Protease | HAI-2 $K_i^{app}$ (nM) ± SD |
|---|---|
| Hepsin | 0.26 ± 0.04 |
| u-PA | >1,000 |

Table 1

| | nM uPA/min |
|---|---|
| control | 1.19 |
| 2D5 | 1.11 |
| 1F2 | 0.87 |
| 1E7 | 1.05 |
| 3H1 | 1.14 |
| 3H10 | 1.12 |
| KD1 | -0.03 |

FIG. 9

MAQKEGGRTVPCCSRPKVAALTAGTLLLTAIGAASWAIVAVLLRSDQEPLYPVQVSSAD
ARLMVFDKTEGTWRLLCSSRSNARVAGLSCEEMGFLRALTHSELDVRTAGANGTSGFFCV
DEGRLPHTQRLLEVISVCDCPRGRFLAAICQDCGRRKLPVDRIVGGRDTSLGRWPWQVSL
RYDGAHLCGGSLLSGDWVLTAAHCFPERNRVLSRWRVFAGAVAQASPHGLQLGVQAVVYH
GGYLPFRDPNSEENSNDIALVHLSSPLPLTEYIQPVCLPAAGQALVDGKICTVTGWGNTQ
YYGQAGVLQEARVPIISNDVCNGADFYGNQIKPKMFCAGYPEGGIDACQGDSGGPFVCE
DSISRTPRWRLCGIVSWGTGCALAQKPGVYTKVSDFREWIFQAIKTHSEASGMVTQL (SEQ ID NO:1)

FIG. 10A

FIG._10B (Illegible sequence listing image)

(SEQ ID NO:2)

METHODS AND COMPOSITIONS FOR TARGETING HEPSIN

CROSS-REFERENCE TO RELATED APPLICATIONS

This application is a National Stage of International Application PCT/US2007/071688, filed Jun. 20, 2007 which claims priority under 35 USC §119 to U.S. Provisional Application No. 60/805,589, filed Jun. 22, 2006, the entire contents of which are hereby incorporated by reference.

FIELD OF THE INVENTION

This invention relates to the field of anti-HEPSIN antibodies, and more particularly to anti-HEPSIN antibodies that are particularly useful for diagnostics and other HEPSIN targeting purposes.

BACKGROUND

Hepsin is a type II transmembrane serine protease (TTSP) expressed on the surface of epithelial cells. The 417-amino acid protein is composed of a short N-terminal cytoplasmic domain, a transmembrane domain and a single scavenger receptor cysteine-rich domain that packs tightly against the C-terminal protease domain (1). The physiologic function of HEPSIN is unclear. Despite its expression in the very early stages of embryogenesis (2), HEPSIN-deficient mice were viable and developed normally (3,4). HEPSIN was found not to be essential for liver regeneration and for coagulation-related physiological functions (3,4). However, HEPSIN has been implicated in ovarian [(5); WO2001/62271] and prostate cancer. Several gene expression studies identified HEPSIN as one of the most highly induced genes in prostate cancer (6-11). Hepsin RNA levels were found to be low in normal prostate and benign hyperplasia, but strongly increased in prostate carcinoma, particularly in advanced stages (8-10). Hepsin protein staining with a monoclonal anti-HEPSIN antibody showed that HEPSIN expression was highest at sites of bone metastasis and in late stage primary tumors (12), which is consistent with the finding that increased HEPSIN RNA levels correlated with higher Gleason grades and tumor progression (7-10,13).

Experimental evidence for a role of HEPSIN in prostate cancer came from a recent study by Klezovitch et al. (14) demonstrating that in a mouse model of non-metastasizing prostate cancer, overexpression of HEPSIN led to primary tumor progression and metastasis. Intriguingly, HEPSIN overexpression was associated with basement membrane disruption (14) pointing towards the possibility that HEPSIN activity is somehow linked to the degradation of basement membrane components. In-vitro, HEPSIN is able to convert the latent growth factor pro-hepatocyte growth factor (pro-HGF) into its active two-chain form (HGF), which induced Met receptor signaling [(15); (16); WO2006/014928]. Because the HGF/Met pathway has been implicated in invasive tumor growth and metastasis, it is possible that overexpression of HEPSIN activates the HGF/Met axis in prostate cancer (15,16). Hepsin was also shown to cleave other substrates in-vitro, mainly coagulation-related proteins (15,17). However, their role in tumorigenesis is not known.

The strong expression of HEPSIN in prostate and other cancers makes it an attractive diagnostic marker for a variety of diseases, in particular cancers. Furthermore, other members of the TTSP family, such as matriptase and TMPRSS2 are shed from cell surfaces and shed matriptase has been detected in human breast milk (18). Based on the structural similarity with these TTSPs, it is possible that tumor-derived HEPSIN could be detected in human body fluids using appropriate detection systems.

It is evident that HEPSIN expression is associated with, and likely plays a role in the etiology of, various diseases. HEPSIN expression is associated with various characteristics of diseases, such as particular stages and extent of malignancy of cancers. One of the most difficult challenges in clinical management of complex diseases such as cancer is the accurate and early identification of the diseases in a patient. Thus, although some antibodies have been generated that apparently bind HEPSIN (e.g., Tsuji et al., J. Biol. Chem. (1991), 266(25):16948-16953; Torres-Rosado et al., Proc. Natl. Acad. Sci. USA (1993), 90:7181-7185; WO2004/035733; WO2002/064839; WO2004/033630), it is clear that it would be beneficial to have compositions and methods that are effective and flexible in detecting and/or targeting HEPSIN in vitro and in vivo. The invention provided herein relate to such compositions and methods.

All references cited herein, including patent applications and publications, are incorporated by reference in their entirety.

DISCLOSURE OF THE INVENTION

The invention provides novel antibodies capable of binding and/or targeting soluble and cell associated HEPSIN protein, in vitro and in vivo. A panel of monoclonal anti-human HEPSIN antibodies were generated that bind to HEPSIN in various forms and at different epitopes. These antibodies have a variety of uses, including use in sensitive detection systems for measuring HEPSIN levels in biological samples.

In one aspect, the invention provides an isolated immunoglobulin polypeptide comprising at least one, two, three, four, five or all hypervariable (HVR) sequences selected from the group consisting of HC-HVR1, HC-HVR2, HC-HVR3, LC-HVR1, LC-HVR2 and LC-HVR3 sequence of an antibody produced by hybridoma cell line deposited at American Type Culture Collection (ATCC) under Accession No. PTA-7469, PTA-7470, PTA-7471, PTA-7472 or PTA-7473, wherein said isolated immunoglobulin polypeptide specifically binds human HEPSIN. For example, in one aspect, the invention provides an isolated antibody comprising at least one, two, three, four, five or all hypervariable (HVR) sequences selected from the group consisting of HC-HVR1, HC-HVR2, HC-HVR3, LC-HVR1, LC-HVR2 and LC-HVR3 sequence of an antibody produced by hybridoma cell line deposited at American Type Culture Collection (ATCC) under Accession No. PTA-7469, PTA-7470, PTA-7471, PTA-7472 or PTA-7473, wherein said isolated antibody specifically binds human HEPSIN. In one embodiment, the invention provides an isolated antibody comprising at least one, two or all HC-HVRs selected from the group consisting of HC-HVR1, HC-HVR2 and HC-HVR3, and at least one, two or all LC-HVRs selected from the group consisting of LC-HVR1, LC-HVR2 and LC-HVR3. In one embodiment, the HVR sequences in an isolated antibody of the invention are those of an antibody produced by hybridoma cell line deposited at American Type Culture Collection (ATCC) under Accession No. PTA-7469. In one embodiment, the HVR sequences in an isolated antibody of the invention are those of an antibody produced by hybridoma cell line deposited at American Type Culture Collection (ATCC) under Accession PTA-7470. In one embodiment, the HVR sequences in an isolated antibody of the invention are those of an antibody produced by hybridoma cell line deposited at American Type Culture Collection (ATCC) under Accession No. PTA-7471. In one embodiment, the HVR sequences in an isolated antibody of the invention are those of an antibody produced by hybridoma cell line deposited at American Type Culture Collection (ATCC) under Accession No. PTA-7472. In one embodiment, the HVR sequences in an isolated antibody of the invention are those of an antibody produced by hybridoma cell line deposited at American Type Culture Collection (ATCC) under Accession No. PTA-7473.

In one aspect, the invention provides an isolated immunoglobulin polypeptide comprising heavy and/or light chain variable domain sequence of an antibody produced by hybridoma cell line deposited at American Type Culture Collection (ATCC) under Accession No. PTA-7469, PTA-7470, PTA-7471, PTA-7472 or PTA-7473, wherein said isolated immunoglobulin polypeptide specifically binds human HEPSIN. For example, in one aspect, the invention provides an isolated antibody comprising heavy and/or light chain variable domain sequence of an antibody produced by hybridoma cell line deposited at American Type Culture Collection (ATCC) under Accession No. PTA-7469, PTA-7470, PTA-7471, PTA-7472 or PTA-7473, wherein said isolated antibody specifically binds human HEPSIN. In one embodiment, the isolated antibody comprises heavy and/or light chain variable domain sequence of an antibody produced by hybridoma cell line deposited at American Type Culture Collection (ATCC) under Accession No. PTA-7469. In one embodiment, the isolated antibody comprises heavy and/or light chain variable domain sequence of an antibody produced by hybridoma cell line deposited at American Type Culture Collection (ATCC) under Accession No. PTA-7470. In one embodiment, the isolated antibody comprises heavy and/or light chain variable domain sequence of an antibody produced by hybridoma cell line deposited at American Type Culture Collection (ATCC) under Accession No. PTA-7471. In one embodiment, the isolated antibody comprises heavy and/or light chain variable domain sequence of an antibody produced by hybridoma cell line deposited at American Type Culture Collection (ATCC) under Accession No. PTA-7472. In one embodiment, the isolated antibody comprises heavy and/or light chain variable domain sequence of an antibody produced by hybridoma cell line deposited at American Type Culture Collection (ATCC) under Accession No. PTA-7473.

In one aspect, the invention provides a monoclonal anti-HEPSIN antibody encoded by an antibody coding sequence of hybridoma cell line deposited at the American Type Culture Collection (ATCC) under Accession No. PTA-7469, PTA-7470, PTA-7471, PTA-7472 or PTA-7473.

In one aspect, the invention provides an isolated monoclonal antibody that binds to the same epitope on human HEPSIN as an antibody produced by hybridoma cell line deposited at American Type Culture Collection (ATCC) under Accession No. PTA-7469, PTA-7470, PTA-7471, PTA-7472 or PTA-7473. In one aspect, the invention provides an isolated antibody that binds to a different epitope on human HEPSIN as any antibody produced by hybridoma cell line deposited at American Type Culture Collection (ATCC) under Accession No. PTA-7469, PTA-7470, PTA-7471, PTA-7472 or PTA-7473.

In one aspect, the invention provides an isolated monoclonal antibody that competes with an antibody produced by hybridoma cell line deposited at American Type Culture Collection (ATCC) under Accession No. PTA-7469, PTA-7470, PTA-7471, PTA-7472 or PTA-7473 for binding to human HEPSIN.

In one embodiment, an antibody of the invention binds specifically to an antigenic determinant or epitope located in an extracellular domain sequence of human HEPSIN. In one embodiment, the extracellular domain sequence comprises $Arg^{45}$ through $Leu^{417}$ of human HEPSIN. In one embodiment, the antigenic determinant or epitope is located in the protease domain of HEPSIN. In one embodiment, an antibody of the invention does not bind specifically to the A chain of HEPSIN.

In one embodiment, an antibody of the invention binds specifically to human HEPSIN but does not substantially inhibit in vivo and/or in vitro HEPSIN enzymatic activity. In one embodiment, the enzymatic activity comprises cleavage of polypeptide substrate of HEPSIN.

In one embodiment of an antibody of the invention, the full length IgG form of the antibody specifically binds human HEPSIN with a binding affinity of about 150 nM or better. In one embodiment, the binding affinity is about 120 nM or better. In one embodiment, the binding affinity is about 100 nM or better. In one embodiment, the binding affinity is about 75 nM or better. In one embodiment, the binding affinity is about 50 nM or better. In one embodiment, the binding affinity is about 25 nM or better. In one embodiment, the binding affinity values are obtained by direct ELISA (e.g., expressed as $EC_{50}$ as measured in direct ELISAs as described in the Examples below).

An antibody of the invention can be in any number of forms. For example, an antibody of the invention can be a monoclonal antibody that is a chimeric antibody, a humanized antibody or a human antibody. An antibody of the invention can be full length or a fragment thereof (e.g., a fragment comprising an antigen binding component).

In one embodiment, an antibody of the invention is not an anti-HEPSIN antibody described in Cancer Research, Volume 66, pages 3611-3619 published in 2006 (e.g., antibody 1A12, 85B11, 94A7, A6, A174, A21 and/or A24 as exemplified in FIG. 4), or an isolated HEPSIN antibody disclosed in PCT Publications WO2004/033630 (e.g., antibody 47A5, 14C7, 46D12, 38E2, 37G10, 31C1, 11C1 and/or 72H6 referred to on page 93 and in FIGS. 15A-D).

In one embodiment, an antibody of the invention does not compete for binding to human HEPSIN with an anti-HEPSIN antibody described in Cancer Research, Volume 66, pages 3611-3619 published in 2006 (e.g., antibody 1A12, 85B11, 94A7, A6, A174, A21 and/or A24 as exemplified in FIG. 4), or an isolated HEPSIN antibody disclosed in PCT Publications WO2004/033630 (e.g., antibody 47A5, 14C7, 46D12, 38E2, 37G10, 31C1, 11C1 and/or 72H6 referred to on page 93 and in FIGS. 15A-D).

In one embodiment, an antibody of the invention does not bind to the same epitope on human HEPSIN as an anti-HEPSIN antibody described in Cancer Research, Volume 66, pages 3611-3619 published in 2006 (e.g., antibody 1A12, 85B11, 94A7, A6, A174, A21 and/or A24 as exemplified in FIG. 4), or an isolated HEPSIN antibody disclosed in PCT Publications WO2004/033630 (e.g., antibody 47A5, 14C7, 46D12, 38E2, 37G10, 31C1, 11C1 and/or 72H6 referred to on page 93 and in FIGS. 15A-D).

In one aspect, the invention provides compositions comprising one or more antibodies of the invention and a carrier. In one embodiment, the carrier is pharmaceutically acceptable.

In one aspect, the invention provides nucleic acids encoding an immunoglobulin polypeptide (e.g., an antibody) of the invention.

In one aspect, the invention provides vectors comprising a nucleic acid of the invention.

In one aspect, the invention provides host cells comprising a nucleic acid or a vector of the invention. A vector can be of any type, for example a recombinant vector such as an expression vector. Any of a variety of host cells can be used. In one embodiment, a host cell is a prokaryotic cell, for example, *E. coli*. In one embodiment, a host cell is a eukaryotic cell, for example a mammalian cell such as Chinese Hamster Ovary (CHO) cell.

In one aspect, the invention provides methods for making an antibody of the invention. For example, the invention provides a method of making an anti-HEPSIN antibody (which, as defined herein includes full length and fragments thereof), said method comprising expressing in a suitable host cell a recombinant vector of the invention encoding said antibody (or fragment thereof), and recovering said antibody.

In one aspect, the invention provides an article of manufacture comprising a container; and a composition contained within the container, wherein the composition comprises one or more antibodies of the invention. In one embodiment, the composition comprises a nucleic acid of the invention. In one embodiment, a composition comprising an immunoglobulin polypeptide (e.g. an antibody) of the invention further comprises a carrier, which in some embodiments is pharmaceutically acceptable. In one embodiment, an article of manufacture of the invention further comprises instructions for administering the composition (e.g., the antibody) to a subject.

In one aspect, the invention provides a kit comprising a first container comprising a composition comprising one or more antibodies of the invention; and a second container comprising a buffer. In one embodiment, the buffer is pharmaceutically acceptable. In one embodiment, a composition comprising an antibody further comprises a carrier, which in some embodiments is pharmaceutically acceptable. In one embodiment, a kit further comprises instructions for using the composition (e.g., the antibody) to detect and/or measure HEPSIN in a sample. In one embodiment, a kit further comprises instructions for administering the composition (e.g., the antibody) to a subject.

In one aspect, an antibody of the invention is linked to a toxin such as a cytotoxic agent. These molecules can be formulated or administered in combination with an additive/enhancing agent, such as a chemotherapeutic agent, radiation or steroid.

In one aspect, the invention provides a method of detecting presence of HEPSIN in a sample, comprising contacting the sample with an antibody of the invention. In one embodiment, binding of the antibody to the sample indicates presence of HEPSIN in the sample.

In one aspect, the invention provides a method of diagnosing a disease comprising determining the level of HEPSIN in a test sample of tissue cells by contacting the sample with an antibody of the invention, whereby HEPSIN bound by the antibody indicates presence and/or amount of HEPSIN in the sample.

In another aspect, the invention provides a method of determining whether an individual is at risk for a disease (e.g., a disease associated with dysregulation of HEPSIN expression) comprising determining the level of HEPSIN in a test sample of tissue cell by contacting the test sample with an antibody of the invention and thereby determining the amount of HEPSIN present in the sample, wherein a higher level of HEPSIN in the test sample, as compared to a control sample comprising normal tissue of the same cell origin as the test sample, is an indication that the individual is at risk for the disease.

In one embodiment of methods of the invention, the level of HEPSIN is determined based on amount of HEPSIN polypeptide indicated by amount of HEPSIN bound by the antibody in the test sample. An antibody employed in the method may optionally be detectably labeled, attached to a solid support, or the like.

In one aspect, the invention provides a method of binding an antibody of the invention to HEPSIN present in a bodily fluid, for example blood.

In yet another aspect, the invention is directed to a method of binding an antibody of the invention to a cell that expresses HEPSIN, wherein the method comprises contacting said cell with said antibody under conditions which are suitable for binding of the antibody to HEPSIN and allowing binding therebetween. In one embodiment, said antibody does not inhibit interaction of HEPSIN with its ligand.

In one aspect, the invention provides a method of targeting an agent (e.g., diagnostic or therapeutic agent) to a HEPSIN-associated tissue in a host, the method comprising administering to the host said agent in a form that is linked to an antibody of the invention, whereby the agent is targeted to the HEPSIN-associated tissue in the host. In one embodiment, the antibody that binds HEPSIN is capable of specifically binding to HEPSIN located on a cell (either in vitro or in vivo), for example where HEPSIN is present on the surface of a cell.

In one aspect, the invention provides a method comprising determining whether a subject comprises a cell that expresses HEPSIN at a level greater than the expression level of HEPSIN in a normal reference sample, wherein presence of said cell indicates that the subject has a disorder associated with dysregulation (e.g., overexpression) of HEPSIN.

In one aspect, the invention provides a method of predicting responsiveness of a subject to therapy for disorder associated with dysregulation (e.g., overexpression) of HEPSIN, said method comprising determining whether the subject comprises a cell that expresses HEPSIN at a level greater than the expression level of HEPSIN in a normal reference sample, wherein presence of said cell indicates that the subject would be responsive to the therapy.

In one aspect, the invention provides a method for monitoring minimal residual disease in a subject treated for a disease associated with dysregulation (e.g., overexpression) of HEPSIN, said method comprising determining whether the subject comprises a cell that expresses HEPSIN at a level greater than the expression level of HEPSIN in a normal reference sample, wherein detection of said cell is indicative of presence of said minimal residual disease.

In one aspect, the invention provides a method for detecting a disease state associated with dysregulation (e.g., overexpression) of HEPSIN in a subject, said method comprising determining whether the subject comprises a cell that expresses HEPSIN at a level greater than the expression level of HEPSIN in a normal reference sample, wherein detection of said cell is indicative of presence of said disease state in the subject.

In one aspect, the invention provides a method for assessing predisposition of a subject to develop a disorder associated with dysregulation (e.g., overexpression) of HEPSIN, said method comprising determining whether the subject comprises a cell that expresses HEPSIN at a level greater than the expression level of HEPSIN in a normal reference sample, wherein detection of said cell is indicative of a predisposition for the subject to develop said disorder.

In one aspect, the invention provides a method for diagnosing a disorder associated with dysregulation (e.g., overexpression) of HEPSIN in a subject, said method comprising determining whether the subject comprises a cell that expresses HEPSIN at a level greater than the expression level of HEPSIN in a normal reference sample, wherein detection of said cell indicates that the subject has said disorder.

In one aspect, the invention provides a method for distinguishing between early and late stage of a disease associated with dysregulation (e.g., overexpression) of HEPSIN (e.g., degree of malignancy, early or advanced stage, etc.) in a subject, said method comprising determining whether the subject comprises a cell that expresses HEPSIN at a level greater than the expression level of HEPSIN in a normal reference sample, wherein detection of said cell indicates that the subject has the late stage of the disease.

In one aspect, the invention provides a method for distinguishing between noninvasive or invasive stage of a disease associated with dysregulation (e.g., overexpression) of HEPSIN in a subject, said method comprising determining whether the subject comprises a cell that expresses HEPSIN at a level greater than the expression level of HEPSIN in a normal reference sample, wherein detection of said cell indicates that the subject has the invasive stage of the disease.

In one aspect, the invention provides a method for distinguishing between nonmetastatic and metastatic stage of a disease associated with dysregulation (e.g., overexpression) of HEPSIN in a subject, said method comprising determining whether the subject comprises a cell that expresses HEPSIN at a level greater than the expression level of HEPSIN in a normal reference sample, wherein detection of said cell indicates that the subject has the metastatic stage of the disease.

The steps in the methods for examining expression of HEPSIN may be conducted in a variety of assay formats, including immunohistochemistry, ELISA and blotting assays. Optionally, the tissue or cell sample comprises disease tissue or cells.

Methods of the invention provide information useful for determining appropriate clinical intervention steps, if and as appropriate. Therefore, in one embodiment of a method of the invention, the method further comprises a clinical intervention step based on results of the assessment of the expression of HEPSIN. For example, appropriate intervention may involve prophylactic and treatment steps, or adjustment(s) of any then-current prophylactic or treatment steps based on HEPSIN expression information obtained by a method of the invention.

Still further methods of the invention include methods of treating a disorder associated with dysregulation (e.g., overexpression) of HEPSIN in a mammal, such as cancer, comprising steps of obtaining tissue or a cell sample from the mammal, examining the tissue or cells for expression (e.g., amount of expression) of HEPSIN, and upon determining said tissue or cell sample expresses HEPSIN (e.g., wherein HEPSIN is expressed in amounts greater than a reference (control) sample), administering an effective amount of a therapeutic agent to said mammal. Optionally, the methods comprise administering an effective amount of a targeted therapeutic agent (e.g., an antibody that binds and/or blocks activity of HEPSIN and/or its corresponding ligand and/or substrate, and a second therapeutic agent (e.g., cytotoxic agent, etc.) to said mammal.

As would be evident to one skilled in the art, in any method of the invention, while detection of increased expression of HEPSIN would positively indicate a characteristic of a disease (e.g., presence, stage or extent of a disease), non-detection of increased expression of HEPSIN would also be informative by providing the reciprocal characterization of the disease.

In one aspect, the invention provides an array/probe set comprising one or more antibodies capable of specifically binding to HEPSIN (e.g., antibodies of the invention).

In one aspect, the invention provides a kit comprising a composition the invention, and instructions for using the composition to detect a disorder associated with dysregulation (e.g., overexpression) of HEPSIN by determining whether expression of HEPSIN is at a level greater than the expression level of HEPSIN in a normal reference sample. In one embodiment, the composition of the invention is an array/probe set comprising one or more antibodies capable of specifically binding to HEPSIN (e.g., antibodies of the invention). In one embodiment, the composition of the invention comprises an antibody that specifically detects HEPSIN. In one embodiment, the composition of the invention comprises an antibody that specifically binds to at least a portion of HEPSIN.

BRIEF DESCRIPTION OF THE DRAWINGS

FIG. 1. Characterization of anti-HEPSIN antibodies.

FIG. 2. $K_i^{app}$ values of inhibition of HEPSIN and uPA by HAI-2.

FIG. 9. One embodiment of an amino acid sequence of native human hepsin.

FIGS. 10A & B. Another embodiment of an amino acid sequence of native human hepsin.

MODES FOR CARRYING OUT THE INVENTION

General Techniques

Figure 3:
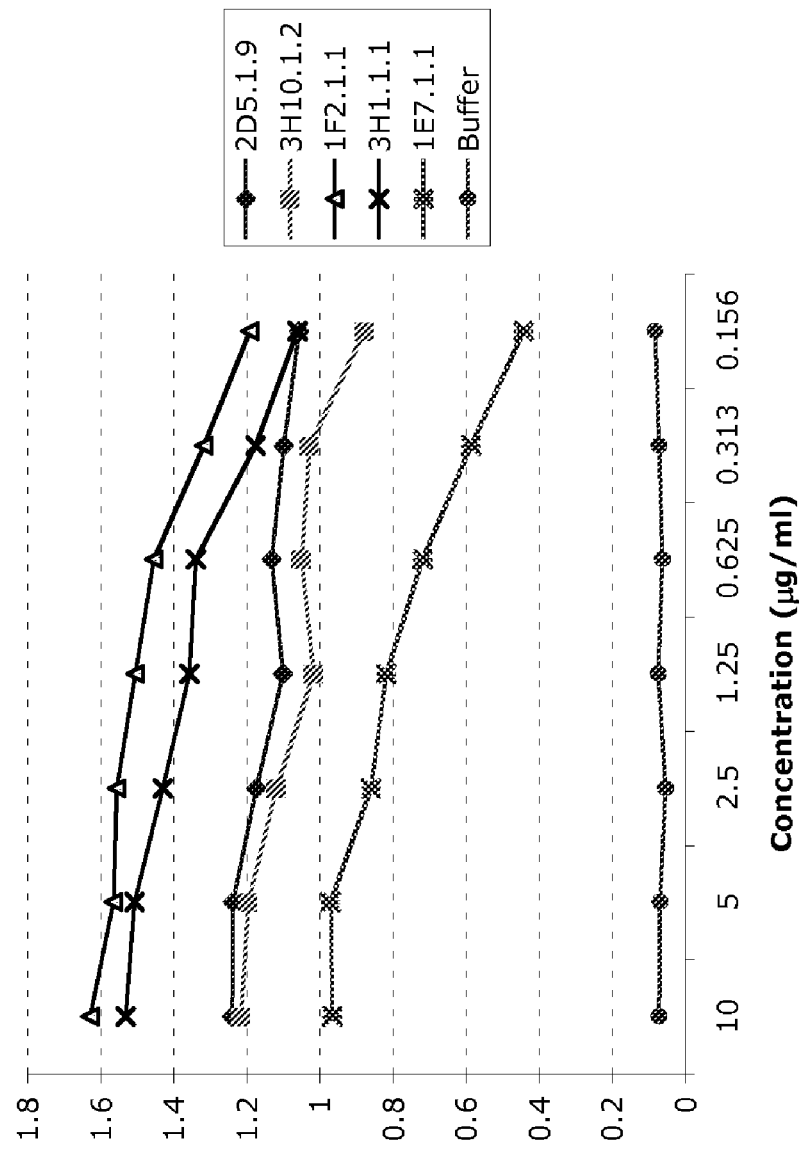
FIG. 3. HEPSIN binding ELISA. Antibodies were added to microtiter plates coated with soluble HEPSIN. Bound antibodies were detected with horseradish-peroxidase conjugated anti-mouse IgG followed by BioFX TMB substrate addition.

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001).

Definitions

The term "HEPSIN" as used herein encompasses native sequence polypeptides, polypeptide variants and fragments of a native sequence polypeptide and polypeptide variants (which are further defined herein) that is capable of pro-HGF cleavage in a manner similar to wild type HEPSIN. The HEPSIN polypeptide described herein may be that which is isolated from a variety of sources, such as from human tissue types or from another source, or prepared by recombinant or synthetic methods. The terms "HEPSIN", "HEPSIN polypeptide", "HEPSIN enzyme", and "HEPSIN protein" also include variants of a HEPSIN polypeptide as disclosed herein.

Figure 10A:
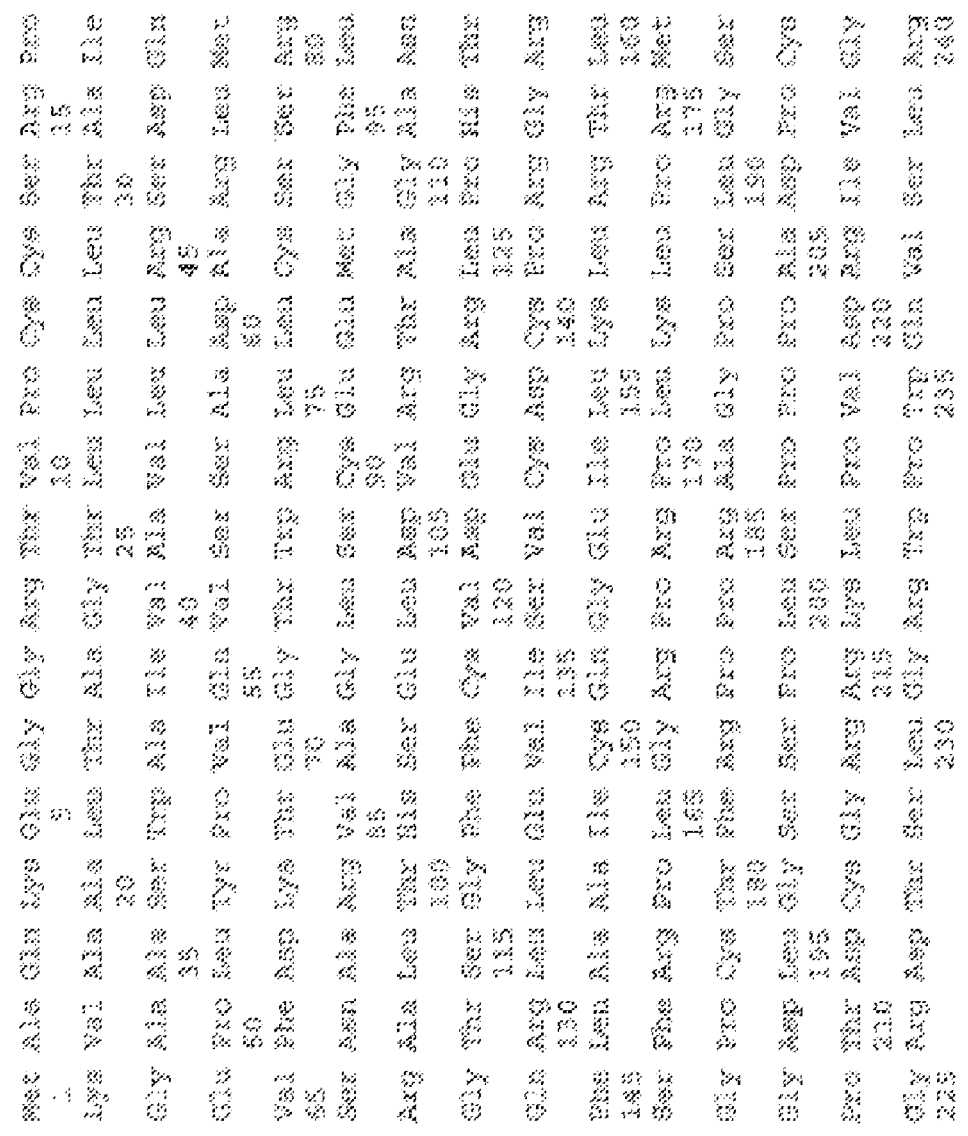

A "native sequence HEPSIN polypeptide" comprises a polypeptide having the same amino acid sequence as the corresponding HEPSIN polypeptide derived from nature. In one embodiment, a native sequence HEPSIN polypeptide comprises the amino acid sequence of SEQ ID NO:1 (see FIG. 9). In one embodiment, a native sequence HEPSIN polypeptide comprises the amino acid sequence of SEQ ID NO:2 (see FIG. 10). Such native sequence HEPSIN polypeptide can be isolated from nature or can be produced by recombinant or synthetic means. The term "native sequence HEPSIN polypeptide" specifically encompasses naturally-occurring truncated or secreted forms of the specific HEPSIN polypeptide (e.g., an extracellular domain sequence), naturally-occurring variant forms (e.g., alternatively spliced forms) and naturally-occurring allelic variants of the polypeptide.

"Hepsin polypeptide variant", or variations thereof, means a HEPSIN polypeptide, generally an active HEPSIN polypeptide, as defined herein having at least about 80% amino acid sequence identity with any of the native sequence HEPSIN polypeptide sequences as disclosed herein. Such HEPSIN polypeptide variants include, for instance, HEPSIN polypeptides wherein one or more amino acid residues are added, or deleted, at the N- or C-terminus of a native amino acid sequence. Ordinarily, a HEPSIN polypeptide variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a native sequence HEPSIN polypeptide sequence as disclosed herein. Ordinarily, HEPSIN variant polypeptides are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, HEPSIN variant polypeptides will have no more than one conservative amino acid substitution as compared to a native HEPSIN polypeptide sequence, alternatively no more than 2, 3, 4, 5, 6, 7, 8, 9, or 10 conservative amino acid substitution as compared to the native HEPSIN polypeptide sequence.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, as described in U.S. Pat. No. 6,828,146.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In one embodiment, the antibody will be purified (1) to greater than 95% by weight of antibody as determined by, for example, the Lowry method, and in some embodiments more than 99% by weight, (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

As used herein, the term "anti-HEPSIN antibody" refers to an antibody that is capable of binding to HEPSIN.

The phrase "substantially similar," "substantially the same", "equivalent", or "substantially equivalent", as used herein, denotes a sufficiently high degree of similarity between two numeric values (for example, one associated with a molecule and the other associated with a reference/comparator molecule) such that one of skill in the art would consider the difference between the two values to be of little or no biological and/or statistical significance within the context of the biological characteristic measured by said values (e.g., Kd values, anti-viral effects, etc.). The difference between said two values is preferably less than about 50%, preferably less than about 40%, preferably less than about 30%, preferably less than about 20%, preferably less than about 10% as a function of the value for the reference/comparator molecule.

The phrase "substantially reduced," or "substantially different", as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd or $IC_{50}$ values). The difference between said two values is preferably greater than about 10%, preferably greater than about 20%, preferably greater than about 30%, preferably greater than about 40%, preferably greater than about 50% as a function of the value for the reference/comparator molecule.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

In one embodiment, the "Kd" or "Kd value" according to this invention is measured by a radiolabeled antigen binding assay (RIA) performed with the Fab version of an antibody of interest and its antigen as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) *J. Mol Biol* 293: 865-881). To establish conditions for the assay, microtiter plates (Dynex) are coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I]-antigen are mixed with serial dilutions of a Fab of interest (e.g., consistent with assessment of an anti-VEGF antibody, Fab-12, in Presta et al., (1997) *Cancer Res.* 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 ul/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment the Kd or Kd value is measured by using surface plasmon resonance assays using a BIAcore™-2000 or a BIAcore™-3000 (BIAcore, Inc., Piscataway, N.J.) at 25C with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen, Y., et al., (1999) *J. Mol Biol* 293:865-881. If the on-rate exceeds $10^6$ $M^{-1}$ $S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stir red cuvette.

An "on-rate" or "rate of association" or "association rate" or "$k_{on}$" according to this invention can also be determined with the same surface plasmon resonance technique described above using a BIAcore™-2000 or a BIAcore™-3000 (BIAcore, Inc., Piscataway, N.J.) at 25C with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of 1M ethanolamine to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) was calculated as the ratio $k_{off}/k_{on}$. See, e.g., Chen, Y., et al., (1999) *J. Mol Biol* 293:865-881. However, if the on-rate exceeds $10^6$ $M^{-1}$ $S^{-1}$ by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a a spectrometer, such as a stop-flow equipped spectrophotometer (Aviv Instruments) or a 8000-series SLM-Aminco spectrophotometer (ThermoSpectronic) with a stirred cuvette. The "Kd" or "Kd value" according to this invention is in one embodiment measured by a radiolabeled antigen binding assay (RIA) performed with the Fab version of the antibody and antigen molecule as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) *J. Mol Biol* 293: 865-881). To establish conditions for the assay, microtiter plates (Dynex) are coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I]-antigen are mixed with serial dilutions of a Fab of interest (consistent with assessement of an anti-VEGF antibody, Fab-12, in Presta et al., (1997) *Cancer Res.* 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature for one hour. The solution is then removed and the plate washed eight times with 0.1% Tween-20 in PBS. When the plates have dried, 150 ul/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment, the Kd or Kd value is measured by using surface plasmon resonance assays using a BIAcore™-2000 or a BIAcore™-3000 (BIAcore, Inc., Piscataway, N.J.) at 25C with immobilized antigen CM5 chips at 10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen, Y., et al., (1999) *J. Mol Biol* 293:865-881. If the on-rate exceeds $10^6$ M$^{-1}$ S$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stir red cuvette.

In one embodiment, an "on-rate" or "rate of association" or "association rate" or "$k_{on}$" according to this invention is determined with the same surface plasmon resonance technique described above using a BIAcore™-2000 or a BIAcore™-3000 (BIAcore, Inc., Piscataway, N.J.) at 25C with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of 1M ethanolamine to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneously fitting the association and dissociation sensorgram. The equilibrium dissociation constant (Kd) was calculated as the ratio $k_{off}/k_{on}$. See, e.g., Chen, Y., et al., (1999) *J. Mol Biol* 293:865-881. However, if the on-rate exceeds $10^6$ M$^{-1}$ S$^{-1}$ by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a a spectrometer, such as a stop-flow equipped spectrophometer (Aviv Instruments) or a 8000-series SLM-Aminco spectrophotometer (ThermoSpectronic) with a stirred cuvette.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

The terms "antibody" and "immunoglobulin" are used interchangeably in the broadest sense and include monoclonal antibodies (e.g., full length or intact monoclonal antibodies), polyclonal antibodies, monovalent, multivalent antibodies, multispecific antibodies (e.g., bispecific antibodies so long as they exhibit the desired biological activity) and may also include certain antibody fragments (as described in greater detail herein). An antibody can be chimeric, human, humanized and/or affinity matured.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., IgG-1, IgG-2, IgA-1, IgA-2, and etc. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

The terms "full length antibody," "intact antibody" and "whole antibody" are used herein interchangeably, to refer to an antibody in its substantially intact form, not antibody fragments as defined below. The terms particularly refer to an antibody with heavy chains that contain the Fc region.

"Antibody fragments" comprise only a portion of an intact antibody, wherein the portion preferably retains at least one, preferably most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise on antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population comprise essentially identical amino acid sequence except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region of the recipient are replaced by residues from a hypervariable region of a non-human species (donor antibody) such as mouse, rat, rabbit or nonhuman primate having the desired specificity, affinity, and/or capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994).

The term "hypervariable region", "HVR", or "HV", when used herein refers to the regions of an antibody variable domain which are hypervariable in sequence and/or form structurally defined loops. The letters "HC" and "LC" preceding the term "HVR" or "HV" refers, respectively, to HVR or HV of a heavy chain and light chain. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
|  |  | (Kabat Numbering) |  |  |
| H1 | H31-H35 | H26-H35 | H26-H32 | H30-H35 |
|  |  | (Chothia Numbering) |  |  |
| H2 | H50-H65 | H50-H58 | H53-H55 | H47-H58 |
| H3 | H95-H102 | H95-H102 | H96-H101 | H93-H101 |

"Framework" or "FR" residues are those variable domain residues other than the hypervariable region residues as herein defined.

The "variable region" or "variable domain" of an antibody refers to the amino-terminal domains of heavy or light chain of the antibody. These domains are generally the most variable parts of an antibody and contain the antigen-binding sites.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more HVRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "blocking" antibody or an "antagonist" antibody is one which inhibits or reduces biological activity of the antigen it binds. Preferred blocking antibodies or antagonist antibodies substantially or completely inhibit the biological activity of the antigen.

An "agonist antibody", as used herein, is an antibody which mimics at least one of the functional activities of a polypeptide of interest.

A "disorder" is any condition that would benefit from treatment. This includes chronic and acute disorders or diseases including those pathological conditions which predispose the mammal to the disorder in question. Non-limiting examples of disorders to be treated herein include cancer and other cell proliferative disorders.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all precancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing or decreasing inflammation and/or tissue/organ damage, decreasing the rate of disease progression, amelioration or palliation of the disease state, and remission or improved prognosis. In some embodiments, antibodies of the invention are used to delay development of a disease or disorder.

An "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule, to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount would be less than the therapeutically effective amount.

The term "cytotoxic agent" as used herein refers to a substance that inhibits or prevents the function of cells and/or causes destruction of cells.

The term "diagnosis" is used herein to refer to the identification of a molecular or pathological state, disease or condition, such as the identification of cell proliferative disorder (e.g., cancer). The term "prognosis" is used herein to refer to the prediction of the likelihood of disorder-attributable disease symptoms, including, for example, recurrence, relapse, and drug resistance, of a disease. The term "prediction" is used herein to refer to the likelihood that a patient will respond either favorably or unfavorably to a drug or set of drugs. In one embodiment, the prediction relates to the extent of those responses. In one embodiment, the prediction relates to whether and/or the probability that a patient will survive or improve following treatment, for example treatment with a particular therapeutic agent, and for a certain period of time without disease recurrence. The predictive methods of the invention can be used clinically to make treatment decisions by choosing the most appropriate treatment modalities for any particular patient. The predictive methods of the present invention are valuable tools in predicting if a patient is likely to respond favorably to a treatment regimen, such as a given therapeutic regimen, including for example, administration of a given therapeutic agent or combination, surgical intervention, steroid treatment, etc., or whether long-term survival of the patient, following a therapeutic regimen is likely.

"Patient response" can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e. reduction, slowing down or complete stopping) of disease spread; (6) decrease of cell proliferation, invasion or metastasis, which may, but does not have to, result in the regression or ablation of a disease lesion; (7) relief, to some extent, of one or more symptoms associated with the disorder; (8) increase in the length of disease-free presentation following treatment; and/or (9) decreased mortality at a given point of time following treatment.

The term "sample", as used herein, refers to a composition that is obtained or derived from a subject of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized.

By "tissue or cell sample" is meant a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

The term "housekeeping gene" refers to a group of genes that codes for proteins whose activities are essential for the maintenance of cell function. These genes are typically similarly expressed in all cell types. Housekeeping genes include, without limitation, glyceraldehyde-3-phosphate dehydrogenase (GAPDH), CypI, albumin, actins, e.g. β-actin, tubulins, cyclophilin, hypoxantine phsophoribosyltransferase (HRPT), L32. 28S, and 18S.

For the purposes herein a "section" of a tissue sample is meant a single part or piece of a tissue sample, e.g. a thin slice of tissue or cells cut from a tissue sample. It is understood that multiple sections of tissue samples may be taken and subjected to analysis according to the present invention, provided that it is understood that the present invention comprises a method whereby the same section of tissue sample is analyzed at both morphological and molecular levels, or is analyzed with respect to both protein and nucleic acid.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of protein binding analysis or protocol, one may use the results of the protein binding analysis or protocol to determine whether a specific therapeutic regimen should be performed.

The word "label" when used herein refers to a compound or composition which is conjugated or fused directly or indirectly to a reagent such as an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable.

General Illustrative Techniques

A sample comprising a target protein can be obtained by methods well known in the art, and that are appropriate for the particular type and location of the disease of interest. Tissue biopsy is often used to obtain a representative piece of disease tissue. Alternatively, cells can be obtained indirectly in the form of tissues/fluids that are known or thought to contain the disease cells of interest. For instance, samples of disease lesions may be obtained by resection, bronchoscopy, fine needle aspiration, bronchial brushings, or from sputum, pleural fluid or blood. Protein targets can be detected from disease tissue or from other body samples such as urine, sputum or serum. The same techniques discussed above for detection of target proteins in disease samples can be applied to other body samples. Disease cells are sloughed off from disease lesions and appear in such body samples. By screening such body samples, a simple early diagnosis can be achieved for these diseases. In addition, the progress of therapy can be monitored more easily by testing such body samples for target proteins.

In one embodiment, methods of the invention are useful for detecting any disorder associated with dysregulation of HEPSIN (e.g., overexpression). The diagnostic methods of the present invention are useful for clinicians so that they can decide upon an appropriate course of treatment. For example, a sample from a subject displaying a high level of expression of HEPSIN disclosed herein might suggest a more aggressive therapeutic regimen than a sample exhibiting a comparatively lower level of expression. Methods of the invention can be utilized in a variety of settings, including for example in aiding in patient selection during the course of drug development, prediction of likelihood of success when treating an individual patient with a particular treatment regimen, in assessing disease progression, in monitoring treatment efficacy, in determining prognosis for individual patients, in assessing predisposition of an individual to develop a particular disorder (e.g., cancer), in differentiating disease staging, etc.

Typical Methods and Assays of the Invention

The methods and assays disclosed herein are directed to the examination of expression of HEPSIN in a mammalian tissue or cell sample, wherein the determination of that expression of HEPSIN is predictive or indicative of whether the tissue or cell sample will be sensitive to treatment based on the use of HEPSIN inhibitors.

As discussed above, there are some populations of diseased human cell types that are associated with abnormal expression of HEPSIN which is associated with various disorders. It is therefore believed that the disclosed methods and assays can provide for convenient, efficient, and potentially cost-effective means to obtain data and information useful in assessing appropriate or effective therapies for treating patients. For example, a patient having been diagnosed with a HEPSIN-related condition could have a biopsy performed to obtain a tissue or cell sample, and the sample could be examined by way of various in vitro assays to determine whether the patient's cells would be sensitive to a therapeutic agent such as a HEPSIN inhibitor (e.g., an anti-HEPSIN antibody).

The invention provides methods for predicting the sensitivity of a mammalian tissue or cell sample (such as a cancer cell) to an anti-HEPSIN inhibitor. In the methods, a mammalian tissue or cell sample is obtained and examined for expression of HEPSIN. The methods may be conducted in a variety of assay formats, including immunohistochemistry assays. Determination of expression of HEPSIN in said tissues or cells will be predictive that such tissues or cells will be sensitive to anti-HEPSIN inhibitor therapy.

As discussed below, expression of HEPSIN in a sample can be analyzed by a number of methodologies, many of which are known in the art and understood by the skilled artisan, including but not limited to, immunohistochemical and/or Western analysis, quantitative blood based assays (as for example serum ELISA) (to examine, for example, levels of protein expression). Typical protocols for evaluating the status of proteins are found, for example in Ausubel et al. eds., 1995, Current Protocols In Molecular Biology, Unit 15 (Immunoblotting), etc.

The protocols below relating to detection of HEPSIN in a sample are provided for illustrative purposes.

Optional methods of the invention include protocols which examine or test for presence of HEPSIN in a mammalian tissue or cell sample. A variety of methods for detecting HEPSIN can be employed and include, for example, immunohistochemical analysis, immunoprecipitation, Western blot analysis, molecular binding assays, ELISA, ELIFA, fluorescence activated cell sorting (FACS) and the like. For example, an optional method of detecting the expression of HEPSIN in a tissue or sample comprises contacting the sample with an antibody of the invention, a HEPSIN-reactive fragment thereof, or a recombinant protein containing an antigen binding region of an antibody of the invention; and then detecting the binding of HEPSIN protein in the sample.

In particular embodiments of the invention, the expression of HEPSIN proteins in a sample is examined using immunohistochemistry and staining protocols. Immunohistochemical staining of tissue sections has been shown to be a reliable method of assessing or detecting presence of proteins in a sample. Immunohistochemistry ("IHC") techniques utilize an antibody to probe and visualize cellular antigens in situ, generally by chromogenic or fluorescent methods.

For sample preparation, a tissue or cell sample from a mammal (typically a human patient) may be used. Examples of samples include, but are not limited to, tissue biopsy, blood, lung aspirate, sputum, lymph fluid, etc. The sample can be obtained by a variety of procedures known in the art including, but not limited to surgical excision, aspiration or biopsy. The tissue may be fresh or frozen. In one embodiment, the sample is fixed and embedded in paraffin or the like.

The tissue sample may be fixed (i.e. preserved) by conventional methodology (See e.g., "Manual of Histological Staining Method of the Armed Forces Institute of Pathology," $3^{rd}$ edition (1960) Lee G. Luna, H T (ASCP) Editor, The Blakston Division McGraw-Hill Book Company, New York; *The Armed Forces Institute of Pathology Advanced Laboratory Methods in Histology and Pathology* (1994) Ulreka V. Mikel, Editor, Armed Forces Institute of Pathology, American Registry of Pathology, Washington, D.C.). One of skill in the art will appreciate that the choice of a fixative is determined by the purpose for which the sample is to be histologically stained or otherwise analyzed. One of skill in the art will also appreciate that the length of fixation depends upon the size of the tissue sample and the fixative used. By way of example, neutral buffered formalin, Bouin's or paraformaldehyde, may be used to fix a sample.

Generally, the sample is first fixed and is then dehydrated through an ascending series of alcohols, infiltrated and embedded with appropriate sectioning media so that the tissue sample may be sectioned. Appropriate sectioning media would include media that permits detection of HEPSIN under desired detection conditions. Alternatively, one may section the tissue and fix the sections obtained. By way of example, the tissue sample may be embedded and processed by conventional methodology (See e.g., "Manual of Histological Staining Method of the Armed Forces Institute of Pathology", supra). Once the tissue sample is embedded, the sample may be sectioned by a microtome or the like (See e.g., "Manual of Histological Staining Method of the Armed Forces Institute of Pathology", supra). By way of example for this procedure, sections may range from about three microns to about five microns in thickness. Once sectioned, the sections may be attached to slides by several standard methods. Examples of slide adhesives include, but are not limited to, silane, gelatin, poly-L-lysine and the like.

Optionally, subsequent to the sample preparation, a tissue section may be analyzed using IHC. IHC may be performed in combination with additional techniques such as morphological staining and/or fluorescence in-situ hybridization. Two general methods of IHC are available; direct and indirect assays. According to the first assay, binding of antibody to the target antigen (e.g., HEPSIN) is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for immunohistochemistry typically will be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in *Current Protocols in Immunology*, Volumes 1 and 2, Coligen et al., Ed. Wiley-Interscience, New York, N.Y., Pubs. (1991) for example and radioactivity can be measured using scintillation counting.

(b) Colloidal gold particles.

(c) Fluorescent labels including, but are not limited to, rare earth chelates (europium chelates), Texas Red, rhodamine, fluorescein, dansyl, Lissamine, umbelliferone, phycocrytherin, phycocyanin, or commercially available fluorophores such SPECTRUM ORANGE7 and SPECTRUM GREEN7 and/or derivatives of any one or more of the above. The fluorescent labels can be conjugated to the antibody using the techniques disclosed in *Current Protocols in Immunology*, supra, for example. Fluorescence can be quantified using a fluorimeter.

(d) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym.* (ed. J. Langone & H. Van Vunakis), Academic press, New York, 73:147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3', 5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase).

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the four broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten and one of the different types of labels mentioned above is conjugated with an anti-hapten antibody. Thus, indirect conjugation of the label with the antibody can be achieved.

Aside from the sample preparation procedures discussed above, further treatment of the tissue section prior to, during or following IHC may be desired. For example, epitope retrieval methods, such as heating the tissue sample in citrate buffer may be carried out (see, e.g., Leong et al. *Appl. Immunohistochem.* 4(3):201 (1996)).

Following an optional blocking step, the tissue section is exposed to primary antibody for a sufficient period of time and under suitable conditions such that the primary antibody binds to the target protein antigen in the tissue sample. Appropriate conditions for achieving this can be determined by routine experimentation. The extent of binding of antibody to the sample is determined by using any one of the detectable labels discussed above. Preferably, the label is an enzymatic label (e.g. HRPO) which catalyzes a chemical alteration of the chromogenic substrate such as 3,3'-diaminobenzidine chromogen. Preferably the enzymatic label is conjugated to antibody which binds specifically to the primary antibody (e.g. the primary antibody is rabbit polyclonal antibody and secondary antibody is goat anti-rabbit antibody).

Optionally, the antibodies employed in the IHC analysis to detect expression of HEPSIN are antibodies generated to bind primarily to HEPSIN, including for example antibodies of the invention. Optionally, the anti-HEPSIN antibody is a monoclonal antibody. Anti-HEPSIN antibodies are readily available in the art, including from various commercial sources, and can also be generated using routine skills known in the art.

Specimens thus prepared may be mounted and coverslipped. Slide evaluation is then determined, e.g. using a microscope, and staining intensity criteria, routinely used in the art, may be employed. As one example, staining intensity criteria may be evaluated as follows:

TABLE A

| Staining Pattern | Score |
|---|---|
| No staining is observed in cells. | 0 |
| Faint/barely perceptible staining is detected in more than 10% of the cells. | 1+ |
| Weak to moderate staining is observed in more than 10% of the cells. | 2+ |
| Moderate to strong staining is observed in more than 10% of the cells. | 3+ |

In alternative methods, the sample may be contacted with an antibody specific for HEPSIN under conditions sufficient for an antibody-HEPSIN complex to form, and then detecting said complex. The presence of HEPSIN may be detected in a number of ways, such as by Western blotting and ELISA procedures for assaying a wide variety of tissues and samples, including plasma or serum. A wide range of immunoassay techniques using such an assay format are available, see, e.g., U.S. Pat. Nos. 4,016,043, 4,424,279 and 4,018,653. These include both single-site and two-site or "sandwich" assays of the non-competitive types, as well as in the traditional competitive binding assays. These assays also include direct binding of a labelled antibody to a target biomarker.

Sandwich assays are among the most useful and commonly used assays. A number of variations of the sandwich assay technique exist, and all are intended to be encompassed by the present invention. Briefly, in a typical forward assay, an unlabelled antibody is immobilized on a solid substrate, and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of HEPSIN.

Variations on the forward assay include a simultaneous assay, in which both sample and labelled antibody are added simultaneously to the bound antibody. These techniques are well known to those skilled in the art, including any minor variations as will be readily apparent. In a typical forward sandwich assay, a first antibody having specificity for the antigen is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g. from room temperature to 40° C. such as between 25° C. and 32° C. inclusive) to allow binding of any subunit present in the antibody. Following the incubation period, the antibody subunit solid phase is washed and dried and incubated with a second antibody specific for a portion of the antigen. The second antibody is linked to a reporter molecule which is used to indicate the binding of the second antibody to the antigen.

An alternative method involves immobilizing the target protein in the sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule. By "reporter molecule", as used in the present specification, is meant a molecule which, by its chemical nature, provides an analytically identifiable signal which allows the detection of antigen-bound antibody. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of target antigen which was present in the sample. Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic color visually detectable with a light microscope. As in the EIA, the fluorescent labelled antibody is allowed to bind to the first antibody-antigen complex. After washing off the unbound reagent, the remaining tertiary complex is then exposed to the light of the appropriate wavelength, the fluorescence observed indicates the presence of the target antigen of interest. Immunofluorescence and EIA techniques are both very well established in the art. However, other reporter molecules, such as radioisotope, chemiluminescent or bioluminescent molecules, may also be employed.

It is contemplated that the above described techniques may also be employed to detect expression of HEPSIN.

Subsequent to the determination that the tissue or cell sample expresses HEPSIN indicating the tissue or cell sample will be sensitive to treatment with HEPSIN inhibitors, it is contemplated that an effective amount of the inhibitor may be administered to the mammal to treat a disorder which is afflicting the mammal. Diagnosis in mammals of the various pathological conditions described herein can be made by the skilled practitioner. Diagnostic techniques are available in the art which allow, e.g., for the diagnosis or detection of disease in a mammal.

A HEPSIN inhibitor can be administered in accordance with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Optionally, administration may be performed through mini-pump infusion using various commercially available devices.

Effective dosages and schedules for HEPSIN inhibitors may be determined empirically, and making such determinations is within the skill in the art. Single or multiple dosages may be employed. For example, an effective dosage or amount of HEPSIN inhibitor used alone may range from about 1 µg/kg to about 100 mg/kg of body weight or more per day. Interspecies scaling of dosages can be performed in a manner known in the art, e.g., as disclosed in Mordenti et al., *Pharmaceut. Res.*, 8:1351 (1991).

When in vivo administration of HEPSIN inhibitor is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

It is contemplated that yet additional therapies may be employed in the methods. The one or more other therapies may include but are not limited to, administration of cytotoxic agents and other standard of care regimens for the particular disorder in question. It is contemplated that such other therapies may be employed as an agent separate from the HEPSIN inhibitor.

For use in the applications described or suggested above, kits or articles of manufacture are also provided by the invention. Such kits may comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be an antibody of the invention.

The kit of the invention will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific therapy or non-therapeutic application, and may also indicate directions for either in vivo or in vitro use, such as those described above.

The kits of the invention have a number of embodiments. A typical embodiment is a kit comprising a container, a label on said container, and a composition contained within said container; wherein the composition includes a primary antibody that binds to HEPSIN, the label on said container indicates that the composition can be used to evaluate the presence of HEPSIN in at least one type of mammalian cell, and instructions for using the antibody for evaluating the presence of HEPSIN in at least one type of mammalian cell. The kit can further comprise a set of instructions and materials for preparing a tissue sample and applying antibody to the same section of a tissue sample. The kit may include both a primary and secondary antibody, wherein the secondary antibody is conjugated to a label, e.g., an enzymatic label.

Other optional components in the kit include one or more buffers (e.g., block buffer, wash buffer, substrate buffer, etc), other reagents such as substrate (e.g., chromogen) which is chemically altered by an enzymatic label, epitope retrieval solution, control samples (positive and/or negative controls), control slide(s) etc.

Antibodies—Generally

In general, anti-HEPSIN antibodies of the invention find utility in a variety of settings, including being used as reagents for detection and isolation of HEPSIN, such as detection of HEPSIN expression in various cell types and tissues, including the determination of HEPSIN density and distribution in cell populations, and cell sorting based on HEPSIN expression. In yet another aspect, the present anti-HEPSIN antibodies are useful for the development of HEPSIN antagonists with binding activity patterns similar to those of the subject antibodies. For example, anti-HEPSIN antibodies of the invention can be used to determine and identify other antibodies that have the same HEPSIN binding characteristics. As a further example, anti-HEPSIN antibodies of the invention can be used to identify other anti-HEPSIN antibodies that bind substantially the same epitope(s) of HEPSIN as the antibodies exemplified herein, including linear and conformational epitopes.

Generation of candidate antibodies can be achieved using routine skills in the art, including those described herein, such as the hybridoma technique and screening of phage displayed libraries of binder molecules. These methods are well-established in the art.

Briefly, the anti-HEPSIN antibodies of the invention can be made by using combinatorial libraries to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the anti-HEPSIN antibodies of the invention can be obtained by designing a suitable antigen screening procedure to select for the phage clone of interest followed by construction of a full length anti-HEPSIN antibody clone using the Fv sequences from the phage clone of interest and suitable constant region (Fc) sequences described in Kabat et al., *Sequences of Proteins of Immunological Interest*, Fifth Edition, NIH Publication 91-3242, Bethesda Md. (1991), vols. 1-3. See also PCT Pub. WO03/102157, and references cited therein.

In one embodiment, anti-HEPSIN antibodies of the invention are monoclonal. Also encompassed within the scope of the invention are antibody fragments such as Fab, Fab', Fab'-SH and F(ab')$_2$ fragments, and variations thereof, of the anti-HEPSIN antibodies provided herein. These antibody fragments can be created by traditional means, such as enzymatic digestion, or may be generated by recombinant techniques. Such antibody fragments may be chimeric, human or humanized. These fragments are useful for the diagnostic and therapeutic purposes set forth herein.

Monoclonal antibodies can be obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

The anti-HEPSIN monoclonal antibodies of the invention can be made using a variety of methods known in the art, including the hybridoma method first described by Kohler et al., *Nature*, 256:495 (1975), or alternatively they may be made by recombinant DNA methods (e.g., U.S. Pat. No. 4,816,567).

Vectors, Host Cells and Recombinant Methods

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin.

Generating Antibodies using Prokaryotic Host Cells

Vector Construction

Polynucleotide sequences encoding polypeptides (antibodies) of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM.TM.-11 may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) *Cell* 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB⁻ strains) provide cytoplasm conditions that are favorable for disulfide bond formation, thereby permitting proper folding and assembly of expressed protein subunits. Proba and Pluckthun *Gene*, 159:203 (1995).

Antibodies of the invention can also be produced by using an expression system in which the quantitative ratio of expressed polypeptide components can be modulated in order to maximize the yield of secreted and properly assembled antibodies of the invention. Such modulation is accomplished at least in part by simultaneously modulating translational strengths for the polypeptide components.

One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence, although silent changes in the nucleotide sequence are preferred. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) *METHODS: A Companion to Methods in Enzymol.* 4:151-158.

Preferably, a set of vectors is generated with a range of TIR strengths for each cistron therein. This limited set provides a comparison of expression levels of each chain as well as the yield of the desired antibody products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in an expression vector construct.

Prokaryotic host cells suitable for expressing antibodies of the invention include *Archaebacteria* and *Eubacteria*, such as Gram-negative or Gram-positive organisms. Examples of useful bacteria include *Escherichia* (e.g., *E. coli*), *Bacilli* (e.g., *B. subtilis*), *Enterobacteria*, *Pseudomonas* species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. In one embodiment, gram-negative cells are used. In one embodiment, *E. coli* cells are used as hosts for the invention. Examples of *E. coli* strains include strain W3110 (Bachmann, *Cellular and Molecular Biology*, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kan$^R$ (U.S. Pat. No. 5,639,635). Other strains and derivatives thereof, such as *E. coli* 294 (ATCC 31,446), *E. coli* B, *E. coli*$_\lambda$ 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., *Proteins*, 8:309-314 (1990). It is generally necessary to select the appropriate bacteria taking into consideration replicability of the replicon in the cells of a bacterium. For example, *E. coli*, *Serratia*, or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., preferably from about 25° C. to about 37° C., preferably at about 30° C. The pH of the medium may be any pH ranging from about 5 to about 9, depending mainly on the host organism. For *E. coli*, the pH can be from about 6.8 to about 7.4, or about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. In one embodiment, the phosphate-limiting medium is the C.R.A.P medium (see, e.g., Simmons et al., *J. Immunol. Methods* (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an $OD_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) *J Bio Chem* 274:19601-19605; Georgiou et al., U.S. Pat. No. 6,083,715; Georgiou et al., U.S. Pat. No. 6,027,888; Bothmann and Pluckthun (2000) *J. Biol. Chem.* 275:17100-17105; Ramm and Pluckthun (2000) *J. Biol. Chem.* 275:17106-17113; Arie et al. (2001) *Mol. Microbiol.* 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., *Microbial Drug Resistance*, 2:63-72 (1996).

In one embodiment, *E. coli* strains deficient for proteolytic enzymes and transformed with plasmids overexpressing one or more chaperone proteins are used as host cells in the expression system of the invention.

Antibody Purification

In one embodiment, an antibody produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the antibody products of the invention. Protein A is a 41 kD cell wall protein from *Staphylococcus aureas* which binds with a high affinity to the Fc region of antibodies. Lindmark et al (1983) *J. Immunol. Meth.* 62:1-13. The solid phase to which Protein A is immobilized can be a column comprising a glass or silica surface, or a controlled pore glass column or a silicic acid column. In some applications, the column is coated with a reagent, such as glycerol, to possibly prevent nonspecific adherence of contaminants.

As the first step of purification, the preparation derived from the cell culture as described above can be applied onto a Protein A immobilized solid phase to allow specific binding of the antibody of interest to Protein A. The solid phase would then be washed to remove contaminants non-specifically bound to the solid phase. Finally the antibody of interest is recovered from the solid phase by elution.

Generating Antibodies using Eukaryotic Host Cells:

The vector components generally include, but are not limited to, one or more of the following: a signal sequence, an origin of replication, one or more marker genes, an enhancer element, a promoter, and a transcription termination sequence.

(i) Signal Sequence Component

A vector for use in a eukaryotic host cell may also contain a signal sequence or other polypeptide having a specific cleavage site at the N-terminus of the mature protein or polypeptide of interest. The heterologous signal sequence selected generally is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication

Generally, an origin of replication component is not needed for mammalian expression vectors. For example, the SV40 origin may typically be used only because it contains the early promoter.

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II (e.g., primate metallothionein genes), adenosine deaminase, ornithine decarboxylase, etc.

For example, cells transformed with the DHFR selection gene may first be identified by culturing all of the transformants in a culture medium that contains methotrexate (Mtx), a competitive antagonist of DHFR. Appropriate host cells when wild-type DHFR is employed include, for example, the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

(iv) Promoter Component

Expression and cloning vectors usually contain a promoter that is recognized by the host organism and is operably linked to nucleic acid encoding a polypeptide of interest (e.g., an antibody). Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Antibody polypeptide transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

(v) Enhancer Element Component

Transcription of DNA encoding an antibody polypeptide of the invention by higher eukaryotes can often be increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the antibody polypeptide-encoding sequence, but is generally located at a site 5' from the promoter.

(vi) Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. patent Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Antibody

When using recombinant techniques, the antibody can be produced intracellularly, or directly secreted into the medium. If the antibody is produced intracellularly, as a first step, the particulate debris, either host cells or lysed fragments, are generally removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a generally acceptable purification technique. The suitability of affinity reagents such as protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to further purification steps, as necessary, for example by low pH hydrophobic interaction chromatography using an elution buffer at a pH between about 2.5-4.5, generally performed at low salt concentrations (e.g., from about 0-0.25M salt).

It should be noted that, in general, techniques and methodologies for preparing antibodies for use in research, testing and clinical use are well-established in the art, consistent with the above and/or as deemed appropriate by one skilled in the art for the particular antibody of interest.

Activity Assays

Antibodies of the invention can be characterized for their physical/chemical properties and biological functions by various assays known in the art.

Purified antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

Where necessary, antibodies are analyzed for their biological activity. In some embodiments, antibodies of the invention are tested for their antigen binding activity. The antigen binding assays that are known in the art and can be used herein include without limitation any direct or competitive binding assays using techniques such as western blots, radioimmunoassays, ELISA (enzyme linked immnosorbent assay), "sandwich" immunoassays, immunoprecipitation assays, fluorescent immunoassays, and protein A immunoassays.

In one embodiment, the invention contemplates an altered antibody that possesses some but not all effector functions, which make it a desirable candidate for many applications in which the half life of the antibody in vivo is important yet certain effector functions (such as complement and ADCC) are unnecessary or deleterious. In certain embodiments, the Fc activities of the antibody are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). An example of an in vitro assay to assess ADCC activity of a molecule of interest is described in U.S. Pat. No. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998). C1q binding assays may also be carried out to confirm that the antibody is unable to bind C1q and hence lacks CDC activity. To assess complement activation, a CDC assay, e.g. as described in Gazzano-Santoro et al., *J. Immunol. Methods* 202:163 (1996), may be performed. FcRn binding and in vivo clearance/half life determinations can also be performed using methods known in the art.

Humanized Antibodies

The invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) *J. Immunol.* 151:2296; Chothia et al. (1987) *J. Mol. Biol.* 196:901. Another method uses a particular framework derived from the consensus sequence of all human antibodies of a particular subgroup of light or heavy chains. The same framework may be used for several different humanized antibodies (Carter et al. (1992) *Proc. Natl. Acad. Sci. USA,* 89:4285; Presta et al. (1993) *J. Immunol.,* 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Antibody Variants

In one aspect, the invention provides antibodies comprising modifications in the interface of Fc polypeptides comprising the Fc region, wherein the modifications facilitate and/or promote heterodimerization. These modifications comprise introduction of a protuberance into a first Fc polypeptide and a cavity into a second Fc polypeptide, wherein the protuberance is positionable in the cavity so as to promote complexing of the first and second Fc polypeptides. Methods of generating antibodies with these modifications are known in the art, e.g., as described in U.S. Pat. No. 5,731,168.

In some embodiments, amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) *Science,* 244: 1081-1085. Here, a residue or group of target residues are identified (e.g., charged residues such as arg, asp, his, lys, and glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table A under the heading of "preferred substitutions". If such substitutions result in a change in biological activity, then more substantial changes, denominated "exemplary substitutions" in Table B, or as further described below in reference to amino acid classes, may be introduced and the products screened.

TABLE B

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):
(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H)

Alternatively, naturally occurring residues may be divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

One type of substitutional variant involves substituting one or more hypervariable region residues of a parent antibody (e.g. a humanized or human antibody). Generally, the resulting variant(s) selected for further development will have modified (e.g., improved) biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to at least part of a phage coat protein (e.g., the gene III product of M13) packaged within each particle. The phage-displayed variants are then screened for their biological activity (e.g. binding affinity) as herein disclosed. In order to identify candidate hypervariable region sites for modification, scanning mutagenesis (e.g., alanine scanning) can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such variants are generated, the panel of variants is subjected to screening using techniques known in the art, including those described herein, and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of antibodies of the invention, thereby generating a Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In accordance with this description and the teachings of the art, it is contemplated that in some embodiments, an antibody of the invention may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter *Nature* 322:738-40 (1988); U.S. Pat. No. 5,648,260; U.S. Pat. No. 5,624,821; and WO94/29351 concerning other examples of Fc region variants.

Immunoconjugates

In another aspect, the invention provides immunoconjugates, or antibody-drug conjugates (ADC), comprising an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10):2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is tested for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is tested for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnology 21(7): 778-784) and are under therapeutic development.

Chemotherapeutic agents useful in the generation of immunoconjugates are described herein (above). Enzymatically active toxins and fragments thereof that can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol)propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolostatins, aurostatins, a trichothecene, and CC1065, and the derivatives of these toxins that have toxin activity, are also contemplated herein.

Maytansine and Maytansinoids

In some embodiments, the immunoconjugate comprises an antibody of the invention conjugated to one or more maytansinoid molecules.

Maytansinoids are mitototic inhibitors which act by inhibiting tubulin polymerization. Maytansine was first isolated from the east African shrub Maytenus serrata (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Exemplary embodiments of maytansinoid drug moieities include: DM1; DM3; and DM4. Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates can be prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and non-patent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. patent application Ser. No. 10/960,602, filed Oct. 8, 2004, the disclosures of which are hereby expressly incorporated by reference. Antibody-maytansinoid conjugates comprising the linker component SMCC may be prepared as disclosed in U.S. patent application Ser. No. 10/960,602, filed Oct. 8, 2004. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio)propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio)propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

Auristatins and Dolostatins

In some embodiments, the immunoconjugate comprises an antibody of the invention conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands", U.S. Ser. No. 10/983,340, filed Nov. 5, 2004, the disclosure of which is expressly incorporated by reference in its entirety.

An exemplary auristatin embodiments are MMAE and MMAF. Additional exemplary embodiments comprising MMAE or MMAF and various linker components (described further herein) Ab-MC-vc-PAB-MMAF, Ab-MC-vc-PAB-MMAE, Ab-MC-MMAE and Ab-MC-MMAF.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; and Pettit et al (1996) J. Chem. Soc. Perkin Trans. 1 5:859-863. See also Doronina (2003) Nat Biotechnol 21(7):778-784; "Monomethylvaline Compounds Capable of Conjugation to Ligands", U.S. Ser. No. 10/983,340, filed Nov. 5, 2004, hereby incorporated by reference in its entirety (disclosing, e.g., linkers and methods of preparing monomethylvaline compounds such as MMAE and MMAF conjugated to linkers).

Calicheamicin

In other embodiments, the immunoconjugate comprises an antibody of the invention conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Preparation of Antibody Drug Conjugates

In the antibody drug conjugates (ADC) of the invention, an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

$$Ab-(L-D)_p \qquad \text{I}$$

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio)pentanoate ("SPP"), N-Succinimidyl 4-(N-maleimidomethyl)cyclohexane-1 carboxylate ("SMCC"), and N-Succinimidyl(4-iodo-acetyl)aminobenzoate ("SIAB"). Additional linker components are known in the art and some are described herein. See also "Monomethylvaline Compounds Capable of Conjugation to Ligands", U.S. Ser. No. 10/983,340, filed Nov. 5, 2004, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Exemplary linker component structures are shown below (wherein the wavy line indicates sites of covalent attachment to other components of the ADC):

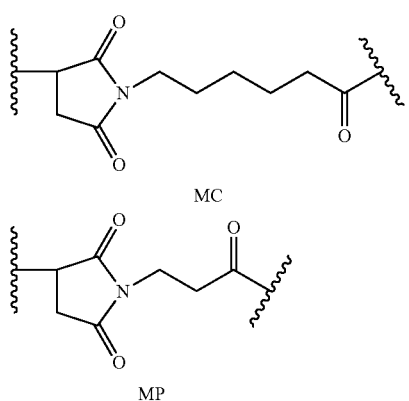
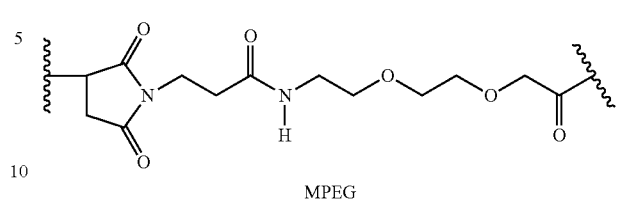
Additional exemplary linker components and abbreviations include (wherein the antibody (Ab) and linker are depicted, and p is 1 to about 8):
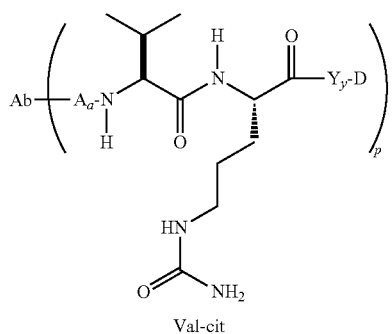
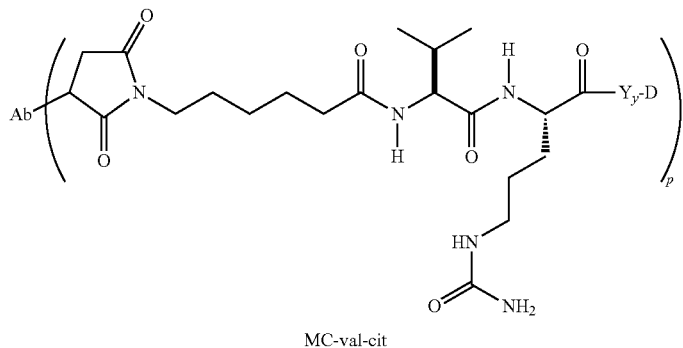
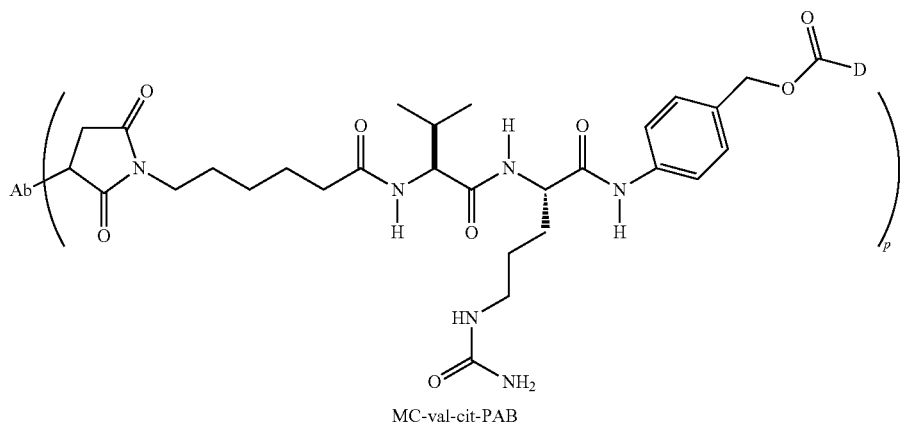

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates of the invention may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Antibody (Ab)-MC-MMAE may be prepared by conjugation of any of the antibodies provided herein with MC-MMAE as follows. Antibody, dissolved in 500 mM sodium borate and 500 mM sodium chloride at pH 8.0 is treated with an excess of 100 mM dithiothreitol (DTT). After incubation at 37° C. for about 30 minutes, the buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm. The reduced antibody dissolved in PBS is chilled on ice. The drug linker reagent, maleimidocaproyl-monomethyl auristatin E (MMAE), i.e. MC-MMAE, dissolved in DMSO, is diluted in acetonitrile and water at known concentration, and added to the chilled reduced antibody 2H9 in PBS. After about one hour, an excess of maleimide is added to quench the reaction and cap any unreacted antibody thiol groups. The reaction mixture is concentrated by centrifugal ultrafiltration and 2H9-MC-MMAE is purified and desalted by elution through G25 resin in PBS, filtered through 0.2 μm filters under sterile conditions, and frozen for storage.

Antibody-MC-MMAF may be prepared by conjugation of any of the antibodies provided herein with MC-MMAF following the protocol provided for preparation of Ab-MC-MMAE.

Antibody-MC-val-cit-PAB-MMAE is prepared by conjugation of any of the antibodies provided herein with MC-val-cit-PAB-MMAE following the protocol provided for preparation of Ab-MC-MMAE.

Antibody-MC-val-cit-PAB-MMAF is prepared by conjugation of any of the antibodies provided herein with MC-val-cit-PAB-MMAF following the protocol provided for preparation of Ab-MC-MMAE.

Antibody-SMCC-DM1 is prepared by conjugation of any of the antibodies provided herein with SMCC-DM1 as follows. Purified antibody is derivatized with (Succinimidyl 4-(N-maleimidomethyl)cyclohexane-1-carboxylate (SMCC, Pierce Biotechnology, Inc) to introduce the SMCC linker. Specifically, antibody is treated at 20 mg/mL in 50 mM potassium phosphate/50 mM sodium chloride/2 mM EDTA, pH 6.5 with 7.5 molar equivalents of SMCC (20 mM in DMSO, 6.7 mg/mL). After stirring for 2 hours under argon at ambient temperature, the reaction mixture is filtered through a Sephadex G25 column equilibrated with 50 mM potassium phosphate/50 mM sodium chloride/2 mM EDTA, pH 6.5. Antibody containing fractions are pooled and assayed.

Antibody-SMCC prepared thus is diluted with 50 mM potassium phosphate/50 mM sodium chloride/2 mM EDTA, pH 6.5, to a final concentration of about 10 mg/ml, and reacted with a 10 mM solution of DM1 in dimethylacetamide. The reaction is stirred at ambient temperature under argon 16.5 hours. The conjugation reaction mixture is filtered through a Sephadex G25 gel filtration column (1.5×4.9 cm) with 1× PBS at pH 6.5. The DM1 drug to antibody ratio (p) may be about 2 to 5, as measured by the absorbance at 252 nm and at 280 nm.

Ab-SPP-DM1 is prepared by conjugation of any of the antibodies provided herein with SPP-DM1 as follows. Purified antibody is derivatized with N-succinimidyl-4-(2-pyridylthio)pentanoate to introduce dithiopyridyl groups. Antibody (376.0 mg, 8 mg/mL) in 44.7 mL of 50 mM potassium phosphate buffer (pH 6.5) containing NaCl (50 mM) and EDTA (1 mM) is treated with SPP (5.3 molar equivalents in 2.3 mL ethanol). After incubation for 90 minutes under argon at ambient temperature, the reaction mixture is gel filtered through a ephadex G25 column equilibrated with 35 mM sodium citrate, 154 mM NaCl, 2 mM EDTA. Antibody containing fractions were pooled and assayed. The degree of modification of the antibody is determined as described above.

Antibody-SPP-Py (about 10 µmoles of releasable 2-thiopyridine groups) is diluted with the above 35 mM sodium citrate buffer, pH 6.5, to a final concentration of about 2.5 mg/mL. DM1 (1.7 equivalents, 17 µmoles) in 3.0 mM dimethylacetamide (DMA, 3% v/v in the final reaction mixture) is then added to the antibody solution. The reaction proceeds at ambient temperature under argon for about 20 hours. The reaction is loaded on a Sephacryl S300 gel filtration column (5.0 cm×90.0 cm, 1.77 L) equilibrated with 35 mM sodium citrate, 154 mM NaCl, pH 6.5. The flow rate may be about 5.0 mL/min and 65 fractions (20.0 mL each) are collected. The number of DM1 drug molecules linked per antibody molecule (p') is determined by measuring the absorbance at 252 nm and 280 nm, and may be about 2 to 4 DM1 drug moities per 2H9 antibody.

Antibody-BMPEO-DM1 is prepared by conjugation of any of the antibodies provided herein with BMPEO-DM1 as follows. The antibody is modified by the bis-maleimido reagent BM(PEO)4 (Pierce Chemical), leaving an unreacted maleimido group on the surface of the antibody. This may be accomplished by dissolving BM(PEO)4 in a 50% ethanol/water mixture to a concentration of 10 mM and adding a tenfold molar excess to a solution containing antibody in phosphate buffered saline at a concentration of approximately 1.6 mg/ml (10 micromolar) and allowing it to react for 1 hour to form antibody-linker intermediate, 2H9-BMPEO. Excess BM(PEO)4 is removed by gel filtration (HiTrap column, Pharmacia) in 30 mM citrate, pH 6 with 150 mM NaCl buffer. An approximate 10 fold molar excess DM1 is dissolved in dimethyl acetamide (DMA) and added to the 2H9-BMPEO intermediate. Dimethyl formamide (DMF) may also be employed to dissolve the drug moiety reagent. The reaction mixture is allowed to react overnight before gel filtration or dialysis into PBS to remove unreacted DM1. Gel filtration on S200 columns in PBS was used to remove high molecular weight aggregates and furnish purified 2H9-BMPEO-DM 1.

Antibody Derivatives

Antibodies of the invention can be further modified to contain additional nonproteinaceous moieties that are known in the art and readily available. In one embodiment, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly (n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

Pharmaceutical Formulations

Therapeutic formulations comprising an antibody of the invention are prepared for storage by mixing the antibody having the desired degree of purity with optional physiologically acceptable carriers, excipients or stabilizers (*Remington's Pharmaceutical Sciences* 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The following are examples of the methods and compositions of the invention. It is understood that various other embodiments may be practiced, given the general description provided above.

EXAMPLE

Materials and Methods

Reagents

Pro-uPA was from Cortex Biochem (San Leandro, Calif.), uPA (high molecular weight form) from American Diagnostica (Greenwich, Conn.) and the chromogenic substrates S2444 and S2366 from Diapharma (Westchester, Ohio). The Kunitz domain inhibitor KD1 derived from hepatocyte growth factor activator inhibitor-1B (HAI-1B) was produced in $E.$ $coli$ as described (19). T.inPro cells were from Expression System LLC (Woodland, Calif.). Nickel-nitrilotriacetic acid resin was from Qiagen Inc (Chatsworth, Calif.) and Q-Sepharose from GE Healthcare (Piscataway, N.J.). A soluble form of hepatocyte growth factor activator inhibitor-2 (HAI-2) was recombinantly expressed and purified as described (16).

A soluble form of HEPSIN comprising the entire extracellular domain was produced by use of a baculovirus expression system. A secreted His-tagged HEPSIN cDNA was constructed by fusion of the cDNA coding for the signal sequence of honey bee melittin (Met$^1$-Tyr$^{20}$) with the cDNA coding for the extracelluar domain of human HEPSIN (Arg$^{45}$-Leu$^{417}$). The final cDNA construct was inserted in a baculovirus expression vector under the control of a polyhedrin promoter and expressed in T.in.Pro cells. Hepsin was purified by nickel-nitrilotriacetic acid affinity chromatography essentially as described (20). Hepsin-containing medium was conditioned with 1 mM sodium azide, 0.3M NaCl and 15 mM Imidazole and the pH was adjusted to pH 6.5 using NaOH. Pre-charged nickel-nitrilotriacetic acid resin was added to media (4 ml resin/1 L medium). Batch absorption was performed by gently stirring at 4° C. for 2 h. After allowing the resin to settle for 1 h, the supernatant was decanted and the resin packed into a column. The column was washed with a minimum of 10 column volumes of PBS/0.3 M NaCl pH 7.4, then followed by 10 column volumes of 25 mM Imidazole, 0.3M NaCl, 1 mM sodium azide pH 8.0. Proteins were eluted with 250 mM Imidazole, 0.3 M NaCl, 1 mM sodium azide pH 8.0. Pooled fractions were diluted 60-fold in 10 mM Tris 1 mM sodium azide pH 8.0 and adjusted to a final pH 8.0 with conductivity below 2.0 mS/cm. The protein was loaded onto Q-Sepharose FF at 0.1 ml resin/mg of protein. The column was washed with a minimum of 10 column volumes of 20 mM Tris, 2 mM sodium azide pH 8.0 and HEPSIN was eluted with a 0-1 M NaCl gradient in 20 mM Tris, 2 mM sodium azide pH 8.0.

Production of Monoclonal Anti-HEPSIN Antibody

Five Balb/c mice (Charles River Laboratories, Mass., USA) were hyperimmunized with purified HEPSIN in RIBI adjuvant (Ribi Immunochem Research Inc., MO, USA). B cells from lymph nodes from five mice were fused with mouse myeloma cells (X63.Ag8.653; American Type Culture Collection, MD, USA) as previously described (21). After 10-14 days, the supernatants were harvested and screened for antibody production with a HEPSIN binding ELISA and by FACS using LnCaP-34 cells and the colorectal cell line HPAC (American Type Culture Collection, Manassas, Va.) as a negative control. Five positive clones, showing the highest immunobinding and specificity after the second round of single cell per well cloning (Elite 1 Sorter, Beckman Coulter, Calif., USA), were scaled up for purification in INTEGRA CELLine 1000 (Integra Biosciences, AG, Switzerland). The supernatants were purified by Protein A affinity chromatography, sterile filtered (0.2 μm pore size; Nalge Nunc International, NY, USA) and stored at 4° C. in PBS.

HEPSIN Binding ELISA

Microtiter plates (Nalge Nunc International, NY, USA) were coated with 100 μl/well of HEPSIN (1 μg/ml) in 0.05 M carbonate buffer, pH 9.6, overnight at 4° C. Plates were washed with PBS/0.05% (v/v) Tween 20 and subsequently blocked with PBS/0.5% (w/v) BSA/0.05% (v/v) Tween 20. 100 μl of culture supernatant was added to each well and incubated for 1 h at RT. Plates were washed and the bound antibody was detected with horseradish peroxidase-conjugated goat anti-mouse IgG (Sigma-Aldrich Inc. MO, USA), 100 μl/well at 1:5000 dilution in PBS/0.5% BSA/0.05% Tween 20, incubated for 30 min. Following an additional wash step, BioFX TMB substrate (BioFX Laboratories, MD, USA) was added, incubated for 5 min and the reaction stopped with BioFX Stop solution (BioFX Laboratories, MD, USA). Then the absorbance at 630 nm was measured on a microplate reader.

Production of HEPSIN Over-Expressing LnCaP Cells

The human prostate carcinoma cell line, LnCaP-FGC (LnCaP), was obtained from American Type Culture Collection (Manassas, Va.). The cells were cultured in RPMI 1640 medium (ATCC, Manassas, Va.) plus 10% fetal bovine serum (Sigma-Aldrich, St. Louis, Mo.). A LnCaP clone that stably expressed the firefly luciferase gene (LnCaP-luc) was used for HEPSIN transfection experiments. To establish the LnCaP-luc cell line the luciferase gene was subcloned as an EcoRI/XhoI cDNA fragment inserted into the pMSCVneo expression vector (BD Biosciences-Clontech, Mountain View, Calif.). LnCaP cells were transfected with the luciferase construct using Lipofectamine 2000 (Invitrogen, Carlsbad, Calif.). The cells were selected with 500 μg/ml Geneticin (Invitrogen) and clones were screened for bioluminescence activity by using the Luclite kit (PerkinElmer, Boston, Mass.). The clone LnCaP-luc, which produced the strongest luminescence signal, was chosen for Hepsin transfection experiments.

The cDNA of full-length HEPSIN was inserted into a mammalian expression vector containing the puromycin resistance gene for antibiotic selection (Genentech, South San Francisco, Calif.). The LnCaP-luc clone was transfected with the construct encoding full-length HEPSIN with a C-terminal Flag tag and the cells were selected with 0.5 μg/ml puromycin (Sigma-Adrich). The clones were analysed by FACS for HEPSIN surface expression using an anti-Flag monoclonal antibody (Sigma-Adrich). Two clones, the high HEPSIN expressor LnCaP-34 and the low HEPSIN expressor LnCaP-17, were selected for studies with the anti-HEPSIN monoclonals.

FACS Analysis

Confluent cell layers were washed with PBS and cells removed with cell dissociation solution (Sigma-Aldrich Inc.

MO, USA). The cells were washed with PBS and resuspended to 0.5–1.0×10$^7$ cells/ml in PBS/1% (v/v) FBS. 100 µl of the cell suspension was incubated with culture supernatants or purified antibodies for 40 min on ice. The cells were washed twice with PBS prior to incubation with PE-conjugated F(ab')$_2$ goat anti-mouse IgG (Jackson Immunoresearch Laboratories Inc. PA, USA) diluted 1:1000 in PBS/1%FBS (v/v). Plates were incubated for 30 min on ice, cells washed twice with PBS. The cell pellets were resuspended in 1% formalin (Richard Allen Scientific, MI, USA) and antibody binding measured on a FACSscan (Becton and Dickinson Biosciences, CA, USA).

Isotyping

The isotypes of the purified MAbs were determined by use of two commercially available kits, the mono-AB-ID SP Kit (Zymed Laboratories, CA, USA) and the mouse monoclonal antibody isotyping kit Isostrip (Roche Diagnostics Corporation, IN, USA).

Biotinylation of Monoclonal Antibodies

Biotin was covalently coupled to IgG via N-hydroxysuccinamide ester of long chain biotin (LCB-NHS, Pierce, USA). The LCB-NHS was dissolved in DMSO (2 mg/ml) and added at a ratio of 100 µg biotin: 1 mg antibody and incubated for 2 h. Free biotin was removed by extensive dialysis against PBS at 4° C. The biotinylated antibodies were then sterile-filtered and stored at 4° C.

Antibody Epitope Determination by Competition Binding ELISA

Microtiter plates were coated with 100 µl/well of HEPSIN (1 µg/ml) in 0.05 M carbonate buffer pH 9.6 overnight at 4° C. The plates were washed with PBS/0.05% (v/v) Tween 20 and blocked with PBS/0.5% BSA/0.05% Tween 20 for 30 min. The unlabeled purified antibodies (20 µg/ml) were incubated for 1 h at RT, followed by the addition of biotinylated antibodies (2 µg/ml). After a 1-h incubation the biotinylated antibody was detected with 1:5000 diluted horseradish peroxidase-conjugated streptavidin (Jackson Immunoresearch Laboratories Inc., PA, USA). The absorbance at 630 nm was measured on a microplate reader.

Pro-uPA Activation by HEPSIN

A soluble form of the bi-Kunitz inhibitor HAI-2 was used as a stop reagent for the pro-uPA activation assay. HAI-2 does potently inhibit HEPSIN activity but not uPA activity as verified in an enzymatic assay. HAI-2 was incubated with 0.5 nM HEPSIN or 10 nM uPA for 30 min in Hepes buffer (20 mM Hepes, pH 7.5, 150 mM NaCl, 5 mM CaCl$_2$, 0.01% Triton X-100) at room temperature. The chromogenic substrates S2366 (for HEPSIN) or S2444 (for uPA) were added at a concentration corresponding to their respective K$_m$ values, which were determined in separate experiments. After substrate addition, the increase in absorbance at 405 nm was measured on a kinetic microplate reader (Molecular Devices, Sunnyvale, Calif.). The K$_i^{app}$ values were determined by fitting the data to the equation for tight binding inhibition (22, 23).

In pro-uPA activation assays, the purified antibodies or KD1 were incubated with HEPSIN for 30 min and the reaction was started by adding pro-uPA. In this mixture the concentration of reactants was as follows: 0.5 nM HEPSIN, 100 nM pro-uPA, 710 nM antibodies and 71 nM KD1. At different time points 50 µl aliquots were removed and added to 0.15 ml HAI-2 in Hepes buffer to stop the reaction. After addition of 50 µl S2444 (2.5 mM), the increase in absorption at 405 nm was measured on a kinetic microplate reader (Molecular Devices, Sunnyvale, Calif.). The concentration of formed uPA at each time point was determined from a standard curve of enzymatically converted pro-uPA and the linear rates of uPA formation calculated. All measurements were carried out at room temperature.

Chromogenic Substrate Assay

The purified antibodies or the HAI-1B derived KD1 inhibitor (19) were incubated with 0.25 nM HEPSIN for 30 min in Hepes buffer. Enzyme activity was monitored after addition of the chromogenic substrate S2366. The final concentrations of the reactants were: 0.25 nM HEPSIN, 500 nM antibody, 50 nM KD1 and 0.25 mM S2366. The increase in absorbance at 405 nm was measured on a kinetic microplate reader and results expressed as fractional enzyme activity ($v_i/v_o$). All measurements were carried out at room temperature.

Immunoblotting

For immunoblotting experiments, recombinant soluble HEPSIN was analyzed by 4-20% SDS-PAGE under reducing conditions. The protein was transferred onto nitrocellulose filters (Invitrogen) using the Bio-Rad Semi Dry Transfer system. HEPSIN was detected by using mouse monoclonal anti-Hepsin antibodies (2D5, 3H10, 1F2, 1E7, 3H1) followed by a HRP-conjugated goat anti-mouse antibody (Pierce; Rockford, Ill.) and ECL (GE Healthcare; Piscataway, N.J.) enhancement.

Results

Figure 4:
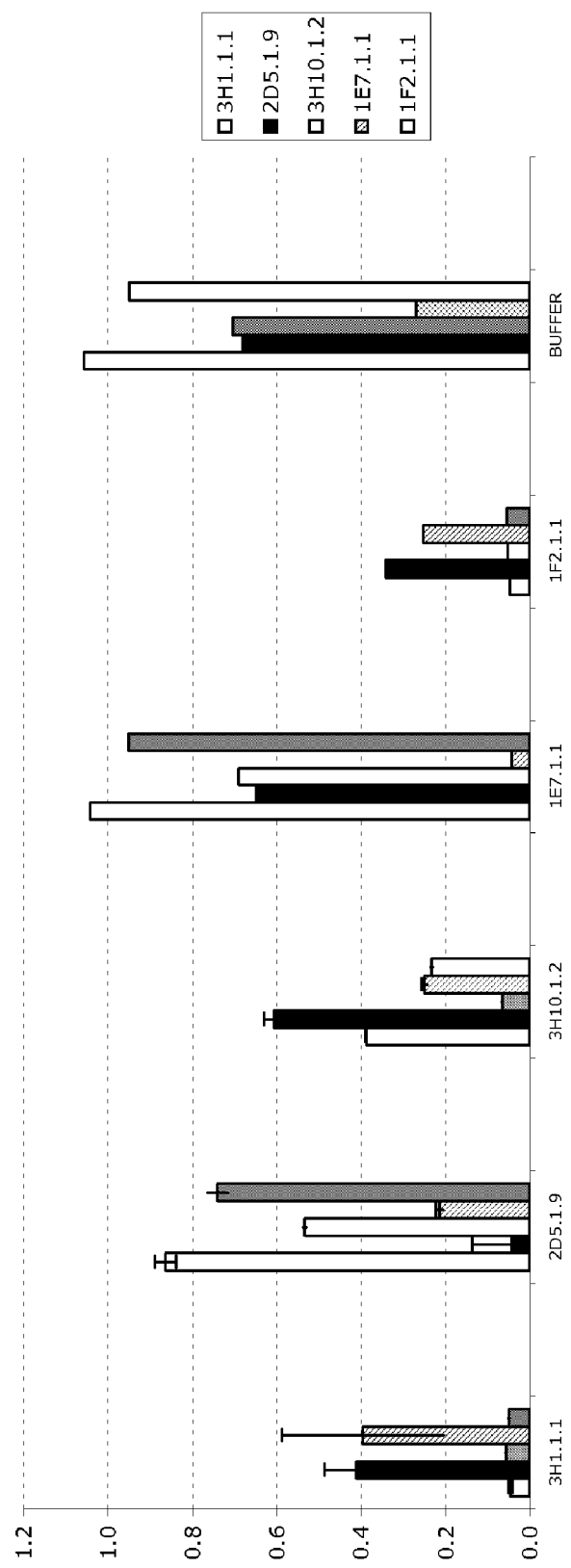
FIG. 4. Epitope determination by competition binding ELISA. Biotinylated antibody and molar excess of unlabelled antibodies were added to microtiter plates coated with soluble HEPSIN. Bound biotinylated antibody was detected with horseradish peroxidase-conjugated streptavidin followed by BioFX TMB substrate addition.
Figure 5:
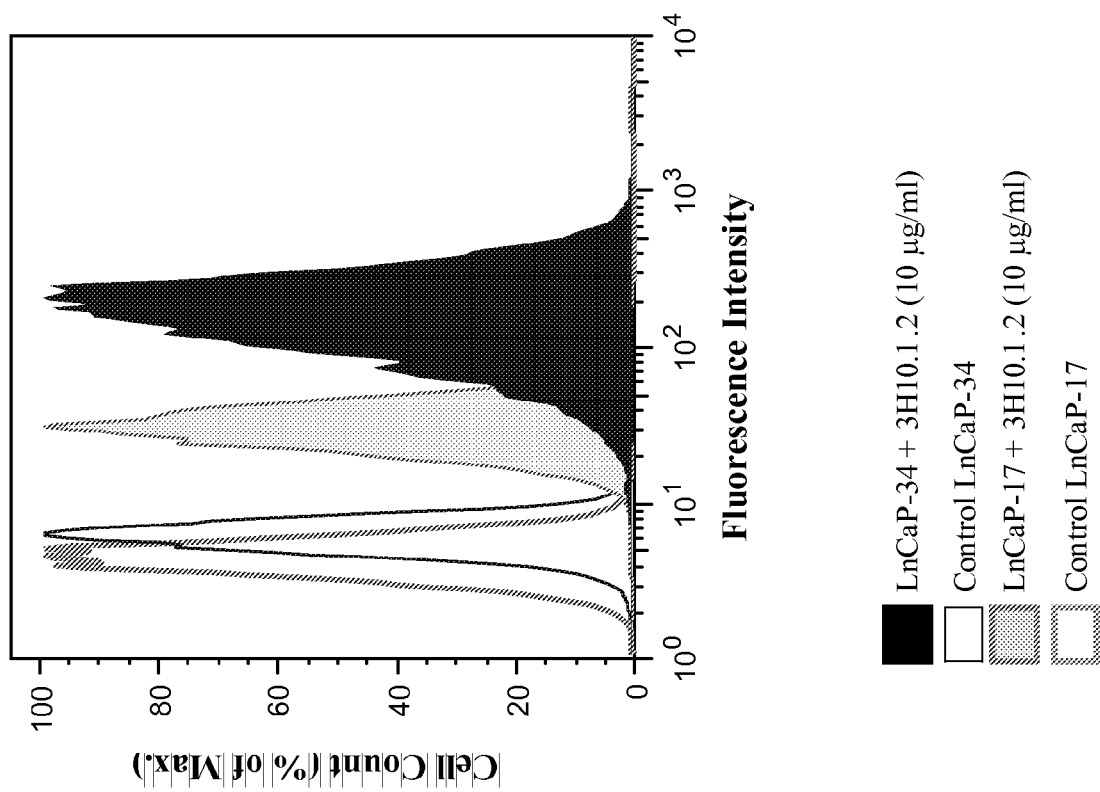
FIG. 5. Histogram of antibody 3H10.1.2 binding to HEPSIN on LnCaP cells. LnCaP-34 cells express transfected HEPSIN and endogenous HEPSIN, while the LnCaP-17 cells only express endogenous HEPSIN. Cell suspensions were incubated with 3H10.1.2 antibody and surface-bound antibody detected with PE-conjugated $F(ab')_2$ anti-mouse IgG on a FACScan. Controls were only incubated with the PE-conjugate.
Figure 6:
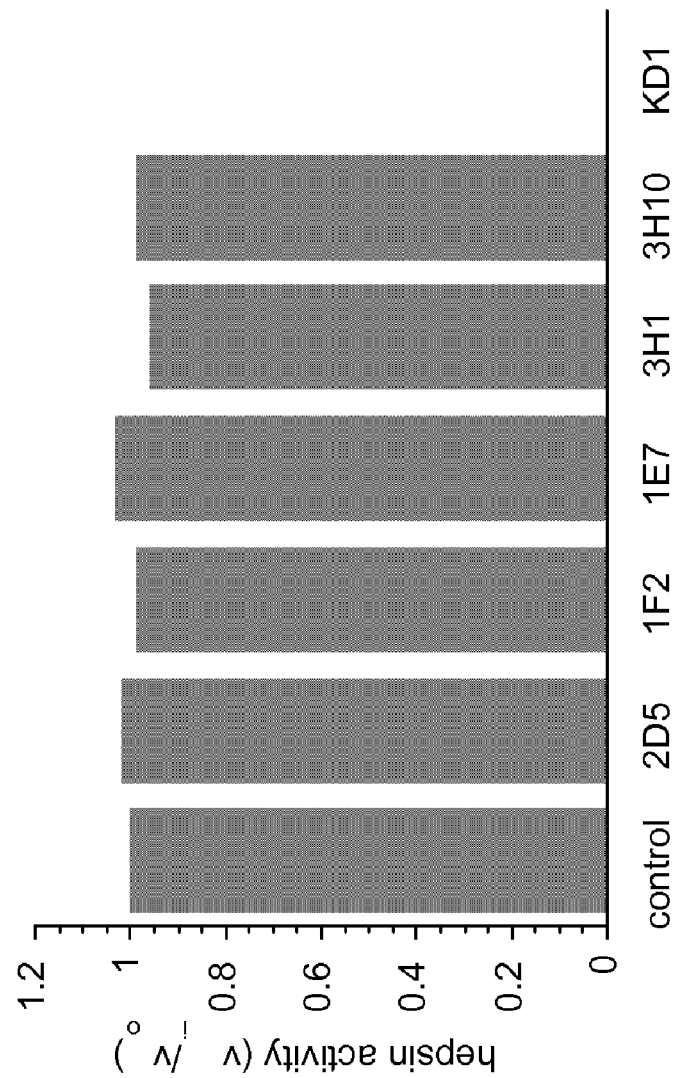
FIG. 6. Chromogenic substrate assay. Antibodies at 500 nM were incubated with soluble HEPSIN (0.25 nM) for 30 min. HEPSIN enzymatic activity towards the para-nitoranilide substrate S2366 was then measured and expressed as fractional activity ($v_i/v_o$). The HEPSIN inhibitor KD1 (50 nM) was used as a positive control.
Figure 7:
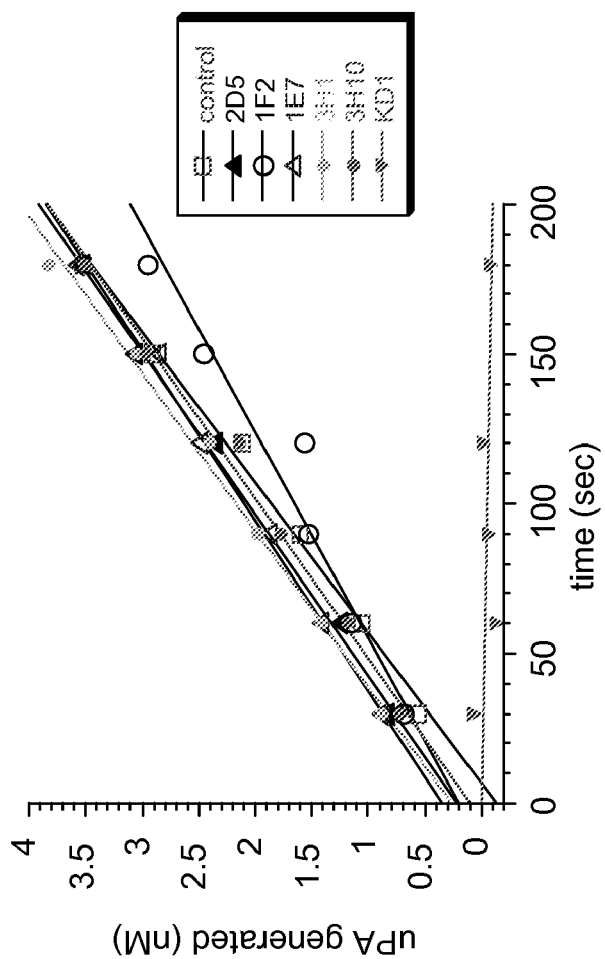
FIG. 7. Pro-uPA activation assay. Antibodies (710 nM) were incubated for 30 min with 0.5 nM HEPSIN and pro-uPA (100 nM) was added to start the reaction. Aliquots were removed at various time points and the concentration of formed uPA determined in the second stage of the assay using the uPA substrate S2444. The rates of uPA formation (Table 1) were calculated from the slopes. The HEPSIN inhibitor KD1 (71 nM) was used as a positive control.

Five monoclonal anti-HEPSIN antibodies were produced. They showed strong binding to HEPSIN in a direct ELISA-type binding assay (FIG. 3). The weakest binder was 1E7.1.1. Cross-blocking experiments were carried out to identify the relative binding epitopes of the antibodies. The antibodies 3H11.1, 3H10.1.2 and 1F2.1.1 inhibited each other from binding to HEPSIN (FIG. 4), indicating that they share a common epitope, referred to as epitope A. 2D5.1.9 and 1E7.1.1 were not inhibited by any of the other antibodies (FIG. 4), indicating that they bind to separate epitopes, which are referred to as epitope B and C, respectively (FIG. 1). The antibody isotypes were determined and are shown in FIG. 1. Two LnCaP cell lines were produced to examine whether the antibodies recognized HEPSIN expressed on cell surfaces. Based on real-time RT-PCR results, we found that the LnCaP-34 cell line overexpressed HEPSIN, while the LnCaP-17 cell line only expressed endogenous levels of HEPSIN (data not shown). FACS analysis of the 5 antibodies showed that they all bound to the cell surfaces. 1E7.1.1 was the weakest binder in agreement with the direct binding ELISA results. Consistent with the higher HEPSIN RNA expression of LnCaP-34 cells, the antibodies gave a stronger fluorescence signal with these cells as indicated by the higher mean fluorescence intensities (FIG. 1). This is exemplified by the histogram in FIG. 5 showing the binding of 3H10.1.2 to the two LnCaP cell lines. The results demonstrated that the antibodies are able to recognize full-length native HEPSIN expressed on the cell surface as well as the recombinant soluble form. Next, we determined whether the antibodies interfered with HEPSIN enzymatic function. In a chromogenic substrate assay with the para-nitroanilide substrate S2366, none of the antibodies interfered with HEPSIN activity at a concentration of 500 nM (FIG. 6). As a positive control we used the potent HEPSIN inhibitor, KD1, which completely inhibited HEPSIN activity at a concentration of 50 nM (FIG. 6). Moreover, the antibodies were examined in a HEPSIN-dependent pro-uPA activation assay. By use of the Kunitz-type inhibitor HAI-2, which potently inhibited HEPSIN but not uPA (FIG. 2), we were able to stop the reaction at different time points and quantify the formed uPA in the second stage of the assay. The linear rates of uPA formation in the presence of antibodies or KD1 are shown in FIG. 7. None of the antibodies significantly inhibited the rate of uPA formation, whereas KD1 completely inhibited the reaction (Table 1 in FIG. 7). These results suggested that the antibodies neither interfere with HEPSIN-mediated activation of small synthetic nor with macromolecular substrates. Therefore, the binding epitopes must be located outside the HEPSIN active site and antibody binding does not allosterically influence the active site conformation, at least not to a degree that would be detrimental to the processing of pro-uPA or S2366 substrates.

Figure 8:
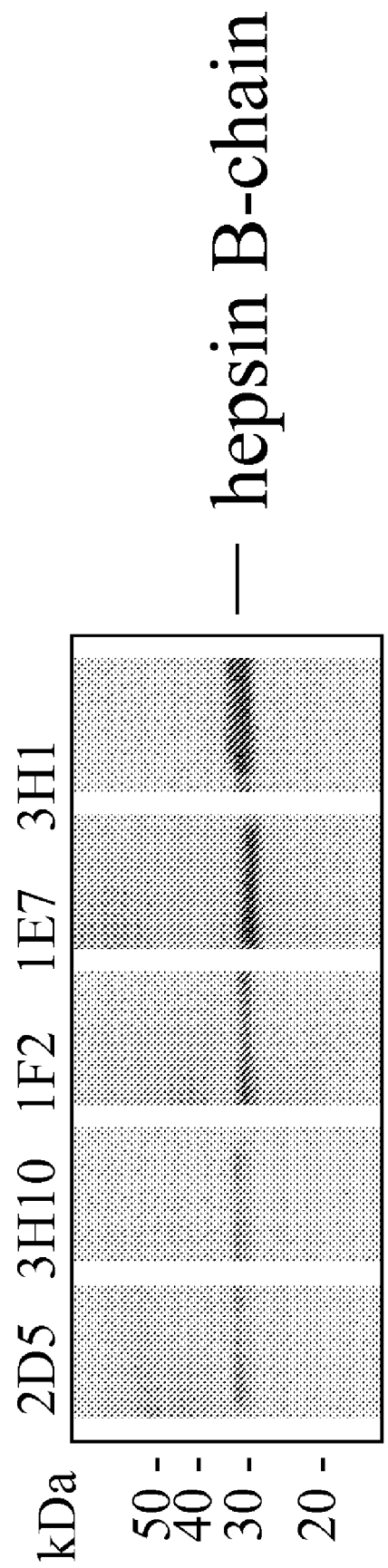
FIG. 8. Immunoblotting of recombinant soluble HEPSIN with monoclonal antibodies. HEPSIN was analyzed by SDS-PAGE under reducing conditions and, after transfer onto nitrocellulose membrane, detected with the anti-HEPSIN monoclonal antibodies. The positions of the HEPSIN B-chain (protease domain) and the molecular weight standards ($M_r \times 10^3$) are indicated.

Immunoblotting experiments showed that the antibodies bound to the 30 kDa protease domain (=B-chain) of HEPSIN (FIG. 8). The 20 kDa A-chain was not detected with the antibodies (FIG. 8) indicating that the binding epitope is contained in the protease domain.

The herein described anti-HEPSIN monoclonal antibodies bind to both soluble and cell surface-expressed HEPSIN. They bind to three distinct epitope regions located on the HEPSIN protease domain. Enzyme kinetics results suggest that they bind outside the active site region, which may allow antibody binding even if the HEPSIN active site is occupied by an endogenous inhibitor. This could be important for the detection of HEPSIN in blood or urine, because tumor-derived HEPSIN may form complexes with endogenous inhibitors similar to matriptase, which was isolated as a matriptase:HAI-1 complex in human breast milk (18). In addition, the ability of the antibodies to bind to denatured or partially denatured HEPSIN may allow detection of tumor-derived HEPSIN that has undergone some degree of degradation and/or denaturation.

The following hybridomas have been deposited with the American Type Culture Collection, 10801 University Boulevard, Manassas, Va. 20110-2209, USA (ATCC):

| Cell Lines | ATCC Accession No. | Deposit Date |
| --- | --- | --- |
| Antibody 4544 (3H10.1.2) | PTA-7472 | Apr. 5, 2006 |
| Antibody 4545 (2D5.1.9) | PTA-7470 | Apr. 5, 2006 |
| Antibody 4546 (1F2.1.1) | PTA-7471 | Apr. 5, 2006 |
| Antibody 4547 (1E7.1.1) | PTA-7473 | Apr. 5, 2006 |
| Antibody 4548 (3H1.1.1) | PTA-7469 | Apr. 5, 2006 |

These deposits were made under the provisions of the Budapest Treaty on the International Recognition of the Deposit of Microorganisms for the Purpose of Patent Procedure and the Regulations thereunder (Budapest Treaty). This assures maintenance of a viable deposit for 30 years from the date of deposit. These cell lines will be made available by ATCC under the terms of the Budapest Treaty, and subject to an agreement between Genentech, Inc. and ATCC, which assures permanent and unrestricted availability of the cell lines to the public upon issuance of the pertinent U.S. patent or upon laying open to the public of any U.S. or foreign patent application, whichever comes first, and assures availability of the cell lines to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the deposited cell lines should be lost or destroyed when cultivated under suitable conditions, they will be promptly replaced on notification with a specimen of the same cell line. Availability of the deposited cell lines is not to be construed as a license to practice the invention in contravention of the rights granted under the authority of any government in accordance with its patent laws.

PARTIAL LIST OF REFERENCES

1. Somoza, J. R., Ho, J. D., Luong, C., Ghate, M., Sprengeler, P. A., Mortara, K., Shrader, W. D., Sperandio, D., Chan, H., McGrath, M. E., and Katz, B. A. (2003) *Structure* 11(9), 1123-1131
2. Vu, T. K., Liu, R. W., Haaksma, C. J., Tomasek, J. J., and Howard, E. W. (1997) *J Biol Chem* 272(50), 31315-31320
3. Yu, I. S., Chen, H. J., Lee, Y. S., Huang, P. H., Lin, S. R., Tsai, T. W., and Lin, S. W. (2000) *Thromb Haemost* 84(5), 865-870
4. Wu, Q., Yu, D., Post, J., Halks-Miller, M., Sadler, J. E., and Morser, J. (1998) *J Clin Invest* 101(2), 321-326
5. Tanimoto, H., Yan, Y., Clarke, J., Korourian, S., Shigemasa, K., Parmley, T. H., Parham, G. P., and O'Brien, T. J. (1997) *Cancer Res* 57(14), 2884-2887
6. Dhanasekaran, S. M., Barrette, T. R., Ghosh, D., Shah, R., Varambally, S., Kurachi, K., Pienta, K. J., Rubin, M. A., and Chinnaiyan, A. M. (2001) *Nature* 412(6849), 822-826
7. Luo, J., Duggan, D. J., Chen, Y., Sauvageot, J., Ewing, C. M., Bittner, M. L., Trent, J. M., and Isaacs, W. B. (2001) *Cancer Res* 61(12), 4683-4688
8. Magee, J. A., Araki, T., Patil, S., Ehrig, T., True, L., Humphrey, P. A., Catalona, W. J., Watson, M. A., and Milbrandt, J. (2001) *Cancer Res* 61(15), 5692-5696
9. Stamey, T. A., Warrington, J. A., Caldwell, M. C., Chen, Z., Fan, Z., Mahadevappa, M., McNeal, J. E., Nolley, R., and Zhang, Z. (2001) *J Urol* 166(6), 2171-2177
10. Stephan, C., Yousef, G. M., Scorilas, A., Jung, K., Jung, M., Kristiansen, G., Hauptmann, S., Kishi, T., Nakamura, T., Loening, S. A., and Diamandis, E. P. (2004) *J Urol* 171(1), 187-191
11. Welsh, J. B., Sapinoso, L. M., Su, A. I., Kern, S. G., Wang-Rodriguez, J., Moskaluk, C. A., Frierson, H. F., Jr., and Hampton, G. M. (2001) *Cancer Res* 61(16), 5974-5978
12. Xuan, J. A., Schneider, D., Toy, P., Lin, R., Newton, A., Zhu, Y., Finster, S., Vogel, D., Mintzer, B., Dinter, H., Light, D., Parry, R., Polokoff, M., Whitlow, M., Wu, Q., and Parry, G. (2006) *Cancer Res* 66(7), 3611-3619
13. Chen, Z., Fan, Z., McNeal, J. E., Nolley, R., Caldwell, M. C., Mahadevappa, M., Zhang, Z., Warrington, J. A., and Stamey, T. A. (2003) *J Urol* 169(4), 1316-1319
14. Klezovitch, O., Chevillet, J., Mirosevich, J., Roberts, R. L., Matusik, R. J., and Vasioukhin, V. (2004) *Cancer Cell* 6(2), 185-195
15. Herter, S., Piper, D. E., Aaron, W., Gabriele, T., Cutler, G., Cao, P., Bhatt, A. S., Choe, Y., Craik, C. S., Walker, N., Meininger, D., Hoey, T., and Austin, R. J. (2005) *Biochem J* 390 (Pt 1), 125-136
16. Kirchhofer, D., Peek, M., Lipari, M. T., Billeci, K., Fan, B., and Moran, P. (2005) *FEBS Lett* 579(9), 1945-1950
17. Kazama, Y., Hamamoto, T., Foster, D. C., and Kisiel, W. (1995) *J Biol Chem* 270(1), 66-72
18. Lin, C. Y., Anders, J., Johnson, M., and Dickson, R. B. (1999) *J Biol Chem* 274(26), 18237-18242
19. Shia, S., Stamos, J., Kirchhofer, D., Fan, B., Wu, J., Corpuz, R. T., Santell, L., Lazarus, R. A., and Eigenbrot, C. (2005) *J Mol Biol* 346(5), 1335-1349
20. Kirchhofer, D., Peek, M., Li, W., Stamos, J., Eigenbrot, C., Kadkhodayan, S., Elliott, J. M., Corpuz, R. T., Lazarus, R. A., and Moran, P. (2003) *J Biol Chem* 278(38), 36341-36349
21. Hongo, J. A., Mora-Worms, M., Lucas, C., and Fendly, B. M. (1995) *Hybridoma* 14(3), 253-260
22. Morrison, J. F. (1969) *Biochim Biophys Acta* 185(2), 269-286
23. Olivero, A. G., Eigenbrot, C., Goldsmith, R., Robarge, K., Artis, D. R., Flygare, J., Rawson, T., Sutherlin, D. P., Kadkhodayan, S., Beresini, M., Elliott, L. O., DeGuzman, G. G., Banner, D. W., Ultsch, M., Marzec, U., Hanson, S. R., Refino, C., Bunting, S., and Kirchhofer, D. (2005) *J Biol Chem* 280(10), 9160-9169

We claim:

1. An isolated antibody comprising (a) the heavy chain hypervariable region (HC-HVR) 1, HC-HVR2, and HC-HVR3 sequences, and (b) the light chain hypervariable region (LC-HVR) 1, LC-HVR2 and LC-HVR3 sequences of an antibody produced by hybridoma cell line deposited at American Type Culture Collection (ATCC) under Accession No. PTA-7469, PTA-7470, PTA-7471, PTA-7472 or PTA-7473, wherein said isolated antibody binds native human sequence HEPSIN polypeptide.

2. An isolated antibody comprising (a) the heavy chain variable domain sequence and/or (b) the light chain variable domain sequence of an antibody produced by hybridoma cell line deposited at American Type Culture Collection (ATCC) under Accession No. PTA-7469, PTA-7470, PTA-7471, PTA-7472 or PTA-7473, wherein said isolated antibody binds native human sequence HEPSIN polypeptide.

3. The antibody of claim 1, wherein the full length IgG form of the antibody specifically binds native human sequence HEPSIN polypeptide with a $EC_{50}$ binding affinity of 150 nM or less.

4. The antibody of claim 3 wherein the $EC_{50}$ binding affinity is 120 nM or less.

5. The antibody of claim 3 wherein the $EC_{50}$ binding affinity is 100 nM or less.

6. The antibody of claim 3 wherein the $EC_{50}$ binding affinity is 75 nM or less.

7. The antibody of claim 3 wherein the $EC_{50}$ binding affinity is 50 nM or less.

8. The antibody of claim 1, wherein the antibody specifically binds native sequence HEPSIN polypeptide that is in native, partially denatured or denatured form.

9. The antibody of claim 1, wherein the antibody binds soluble or cell-attached native sequence HEPSIN polypeptide.

10. An anti-HEPSIN antibody encoded by the antibody coding sequence of hybridoma cell line deposited at the American Type Culture Collection (ATCC) under Accession No. PTA-7469, PTA-7470, PTA-7471, PTA-7472 or PTA-7473.

11. A nucleic acid molecule comprising a nucleic acid sequence encoding the antibody of claim 1.

12. A host cell comprising the nucleic acid molecule of claim 11.

13. A cell line capable of producing the antibody of claim 1.

14. A method of producing the antibody of claim 1, comprising culturing a host cell comprising a nucleic acid encoding the antibody under conditions wherein the antibody is produced.

15. A composition comprising the antibody of claim 1, and a carrier.

16. A method of detecting presence of native sequence HEPSIN polypeptide in a sample, comprising contacting the sample with an antibody of claim 1 and diagnosing presence of native sequence HEPSIN polypeptide by detecting binding of the antibody to HEPSIN polypeptide, wherein detection of binding indicates the presence of native sequence HEPSIN polypeptide.

* * * * *

SEQUENCE LISTING

<160> NUMBER OF SEQ ID NOS: 2

<210> SEQ ID NO 1
<211> LENGTH: 417
<212> TYPE: PRT
<213> ORGANISM: Homo sapiens

<400> SEQUENCE: 1

```
Met Ala Gln Lys Glu Gly Gly Arg Thr Val Pro Cys Cys Ser Arg
 1               5                  10                  15

Pro Lys Val Ala Ala Leu Thr Ala Gly Thr Leu Leu Leu Leu Thr
                20                  25                  30

Ala Ile Gly Ala Ala Ser Trp Ala Ile Val Ala Val Leu Leu Arg
                35                  40                  45

Ser Asp Gln Glu Pro Leu Tyr Pro Val Gln Val Ser Ser Ala Asp
                50                  55                  60

Ala Arg Leu Met Val Phe Asp Lys Thr Glu Gly Thr Trp Arg Leu
                65                  70                  75

Leu Cys Ser Ser Arg Ser Asn Ala Arg Val Ala Gly Leu Ser Cys
                80                  85                  90

Glu Glu Met Gly Phe Leu Arg Ala Leu Thr His Ser Glu Leu Asp
                95                 100                 105

Val Arg Thr Ala Gly Ala Asn Gly Thr Ser Gly Phe Phe Cys Val
               110                 115                 120

Asp Glu Gly Arg Leu Pro His Thr Gln Arg Leu Leu Glu Val Ile
               125                 130                 135

Ser Val Cys Asp Cys Pro Arg Gly Arg Phe Leu Ala Ala Ile Cys
               140                 145                 150

Gln Asp Cys Gly Arg Arg Lys Leu Pro Val Asp Arg Ile Val Gly
               155                 160                 165

Gly Arg Asp Thr Ser Leu Gly Arg Trp Pro Trp Gln Val Ser Leu
               170                 175                 180

Arg Tyr Asp Gly Ala His Leu Cys Gly Gly Ser Leu Leu Ser Gly
               185                 190                 195

Asp Trp Val Leu Thr Ala Ala His Cys Phe Pro Glu Arg Asn Arg
               200                 205                 210

Val Leu Ser Arg Trp Arg Val Phe Ala Gly Ala Val Ala Gln Ala
               215                 220                 225

Ser Pro His Gly Leu Gln Leu Gly Val Gln Ala Val Val Tyr His
               230                 235                 240

Gly Gly Tyr Leu Pro Phe Arg Asp Pro Asn Ser Glu Glu Asn Ser
               245                 250                 255

Asn Asp Ile Ala Leu Val His Leu Ser Ser Pro Leu Pro Leu Thr
               260                 265                 270

Glu Tyr Ile Gln Pro Val Cys Leu Pro Ala Ala Gly Gln Ala Leu
               275                 280                 285

Val Asp Gly Lys Ile Cys Thr Val Thr Gly Trp Gly Asn Thr Gln
               290                 295                 300

Tyr Tyr Gly Gln Gln Ala Gly Val Leu Gln Glu Ala Arg Val Pro
               305                 310                 315

Ile Ile Ser Asn Asp Val Cys Asn Gly Ala Asp Phe Tyr Gly Asn
               320                 325                 330

Gln Ile Lys Pro Lys Met Phe Cys Ala Gly Tyr Pro Glu Gly Gly
               335                 340                 345
```

```
Ile Asp Ala Cys Gln Gly Asp Ser Gly Gly Pro Phe Val Cys Glu
                350                 355                 360

Asp Ser Ile Ser Arg Thr Pro Arg Trp Arg Leu Cys Gly Ile Val
                365                 370                 375

Ser Trp Gly Thr Gly Cys Ala Leu Ala Gln Lys Pro Gly Val Tyr
                380                 385                 390

Thr Lys Val Ser Asp Phe Arg Glu Trp Ile Phe Gln Ala Ile Lys
                395                 400                 405

Thr His Ser Glu Ala Ser Gly Met Val Thr Gln Leu
                410                 415

<210> SEQ ID NO 2
<211> LENGTH: 476
<212> TYPE: PRT
<213> ORGANISM: Homo sapiens

<400> SEQUENCE: 2

Met Ala Gln Lys Glu Gly Gly Arg Thr Val Pro Cys Cys Ser Arg
 1               5                  10                  15

Pro Lys Val Ala Ala Leu Thr Ala Gly Thr Leu Leu Leu Leu Thr
                20                  25                  30

Ala Ile Gly Ala Ala Ser Trp Ala Ile Val Ala Val Leu Leu Arg
                35                  40                  45

Ser Asp Gln Glu Pro Leu Tyr Pro Val Gln Val Ser Ser Ala Asp
                50                  55                  60

Ala Arg Leu Met Val Phe Asp Lys Thr Glu Gly Thr Trp Arg Leu
                65                  70                  75

Leu Cys Ser Ser Arg Ser Asn Ala Arg Val Ala Gly Leu Ser Cys
                80                  85                  90

Glu Glu Met Gly Phe Leu Arg Ala Leu Thr His Ser Glu Leu Asp
                95                  100                 105

Val Arg Thr Ala Gly Ala Asn Gly Thr Ser Gly Phe Phe Cys Val
                110                 115                 120

Asp Glu Gly Arg Leu Pro His Thr Gln Arg Leu Leu Glu Val Ile
                125                 130                 135

Ser Val Cys Asp Cys Pro Arg Gly Arg Phe Leu Ala Ala Ile Cys
                140                 145                 150

Gln Gly Glu Ile Leu Lys Leu Arg Thr Leu Ser Phe Arg Pro Leu
                155                 160                 165

Gly Arg Pro Arg Pro Leu Lys Leu Pro Arg Met Gly Pro Cys Thr
                170                 175                 180

Phe Arg Pro Pro Arg Ala Gly Pro Ser Leu Gly Ser Gly Asp Leu
                185                 190                 195

Gly Ser Ser Pro Leu Ser Pro Pro Ala Asp Pro Cys Pro Thr
                200                 205                 210

Asp Cys Gly Arg Arg Lys Leu Pro Val Asp Arg Ile Val Gly Gly
                215                 220                 225

Arg Asp Thr Ser Leu Gly Arg Trp Pro Trp Gln Val Ser Leu Arg
                230                 235                 240

Tyr Asp Gly Ala His Leu Cys Gly Gly Ser Leu Leu Ser Gly Asp
                245                 250                 255

Trp Val Leu Thr Ala Ala His Cys Phe Pro Glu Arg Asn Arg Val
                260                 265                 270

Leu Ser Arg Trp Arg Val Phe Ala Gly Ala Val Ala Gln Ala Ser
                275                 280                 285
```

```
-continued

Pro His Gly Leu Gln Leu Gly Val Gln Ala Val Val Tyr His Gly
                 290                 295                 300

Gly Tyr Leu Pro Phe Arg Asp Pro Asn Ser Glu Asn Ser Asn
                 305                 310                 315

Asp Ile Ala Leu Val His Leu Ser Ser Pro Leu Pro Leu Thr Glu
                 320                 325                 330

Tyr Ile Gln Pro Val Cys Leu Pro Ala Ala Gly Gln Ala Leu Val
                 335                 340                 345

Asp Gly Lys Ile Cys Thr Val Thr Gly Trp Gly Asn Thr Gln Tyr
                 350                 355                 360

Tyr Gly Gln Gln Ala Gly Val Leu Gln Glu Ala Arg Val Pro Ile
                 365                 370                 375

Ile Ser Asn Asp Val Cys Asn Gly Ala Asp Phe Tyr Gly Asn Gln
                 380                 385                 390

Ile Lys Pro Lys Met Phe Cys Ala Gly Tyr Pro Glu Gly Gly Ile
                 395                 400                 405

Asp Ala Cys Gln Gly Asp Ser Gly Gly Pro Phe Val Cys Glu Asp
                 410                 415                 420

Ser Ile Ser Arg Thr Pro Arg Trp Arg Leu Cys Gly Ile Val Ser
                 425                 430                 435

Trp Gly Thr Gly Cys Ala Leu Ala Gln Lys Pro Gly Val Tyr Thr
                 440                 445                 450

Lys Val Ser Asp Phe Arg Glu Trp Ile Phe Gln Ala Ile Lys Thr
                 455                 460                 465

His Ser Glu Ala Ser Gly Met Val Thr Gln Leu
                 470                 475
```